United States Patent
Tassone et al.

(10) Patent No.: US 9,404,111 B2
(45) Date of Patent: Aug. 2, 2016

(54) INHIBITORS OF MIRNAS 221 AND 222 FOR ANTI-TUMOR ACTIVITY IN MULTIPLE MYELOMA

(71) Applicants: Pierfrancesco Tassone, Catanzaro (IT); Pierosandro Tagliaferri, Naples (IT); Maria Teresa Di Martino, Catanzaro (IT)

(72) Inventors: Pierfrancesco Tassone, Catanzaro (IT); Pierosandro Tagliaferri, Naples (IT); Maria Teresa Di Martino, Catanzaro (IT)

( * ) Notice: Subject to any disclaimer, the term of this patent is extended or adjusted under 35 U.S.C. 154(b) by 0 days.

(21) Appl. No.: 14/798,660

(22) Filed: Jul. 14, 2015

(65) Prior Publication Data

US 2015/0361433 A1 Dec. 17, 2015

Related U.S. Application Data

(63) Continuation of application No. PCT/IB2013/050328, filed on Jan. 14, 2013.

(51) Int. Cl.
| | | |
|---|---|---|
| C07H 21/02 | (2006.01) |
| C07H 21/04 | (2006.01) |
| A61K 48/00 | (2006.01) |
| C12N 15/113 | (2010.01) |

(52) U.S. Cl.
CPC .......... *C12N 15/1135* (2013.01); *C12N 15/113* (2013.01); *C12N 2310/113* (2013.01); *C12N 2310/14* (2013.01); *C12N 2310/315* (2013.01); *C12N 2310/3231* (2013.01); *C12N 2310/346* (2013.01)

(58) Field of Classification Search
CPC .............................. A61K 48/00; C12N 15/113
See application file for complete search history.

(56) References Cited

PUBLICATIONS

Roccaro, et al., "MicroRNAs 15a and 16 regulate tumor proliferation in multiple myeloma", Blood, vol. 113, No. 26, Jun. 25, 2009, pp. 6669-6680.
Zhao, et al., "Mir-22-221 induce Dexamethasone resistance by targeting BBC3/PUMA in human multiple myeloma", Blood, vol. 118, No. 21, Nov. 2011, p. 617.
Pineau, et al., "miR-221 overexpression contributes to liver tumorigenesis", Proceedings of the National Academy of Sciences of the United States of America, vol. 107, No. 1, Jan. 2010, pp. 264-269.
Park, et al., "miR-221 silencing blocks hepatocellular carcinoma and promotes survival", Cancer Research, vol. 71, No. 24, Dec. 15, 2011, pp. 7608-7616.
International Search Report and Written Opinion in counterpart application PCT/IB2013/050328 dated Sep. 4, 2013.

*Primary Examiner* — Amy Bowman
(74) *Attorney, Agent, or Firm* — Stradley Ronon Stevens & Young, LLP

(57) ABSTRACT

Inhibitors of miRNAs 221 and 222, and their use as medicaments in the treatment of multiple myeloma. The inhibitors inhibit miRNAs 221 and 222 of the type of LNA-miRNAs and have the formula +C*A*G*+A*+C*A*+A*T*+G*T*+A*+G*C, and formula C*+A*+G*+A*T*+G*T*+A*+G*C wherein letters with symbol "+" indicate the positions of LNA and symbol "*" indicates phosphorothioate bonds.

16 Claims, 12 Drawing Sheets

A

B

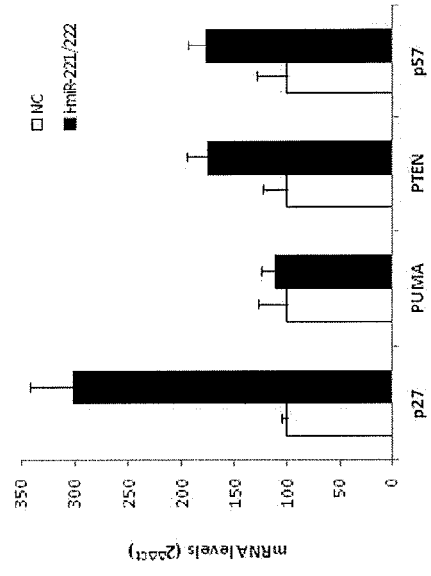
FIGURE 3B
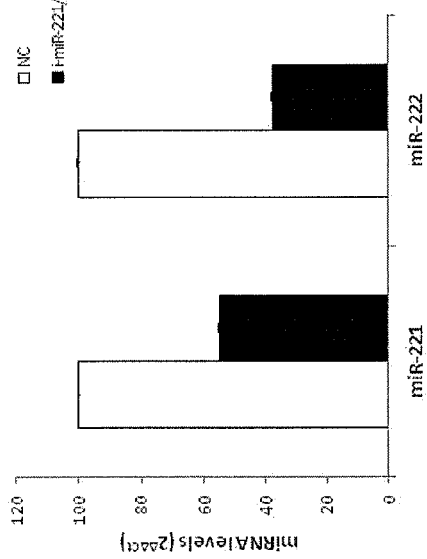
FIGURE 3D
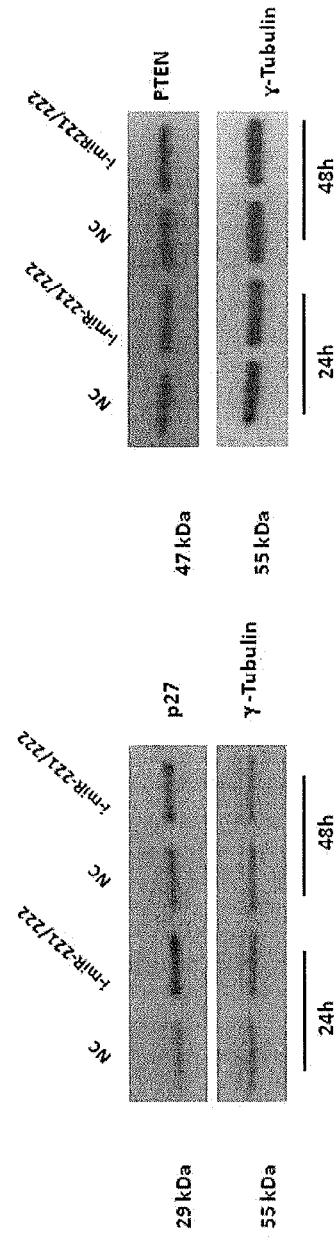
FIGURE 3C
FIGURE 3E

FIGURE 6C
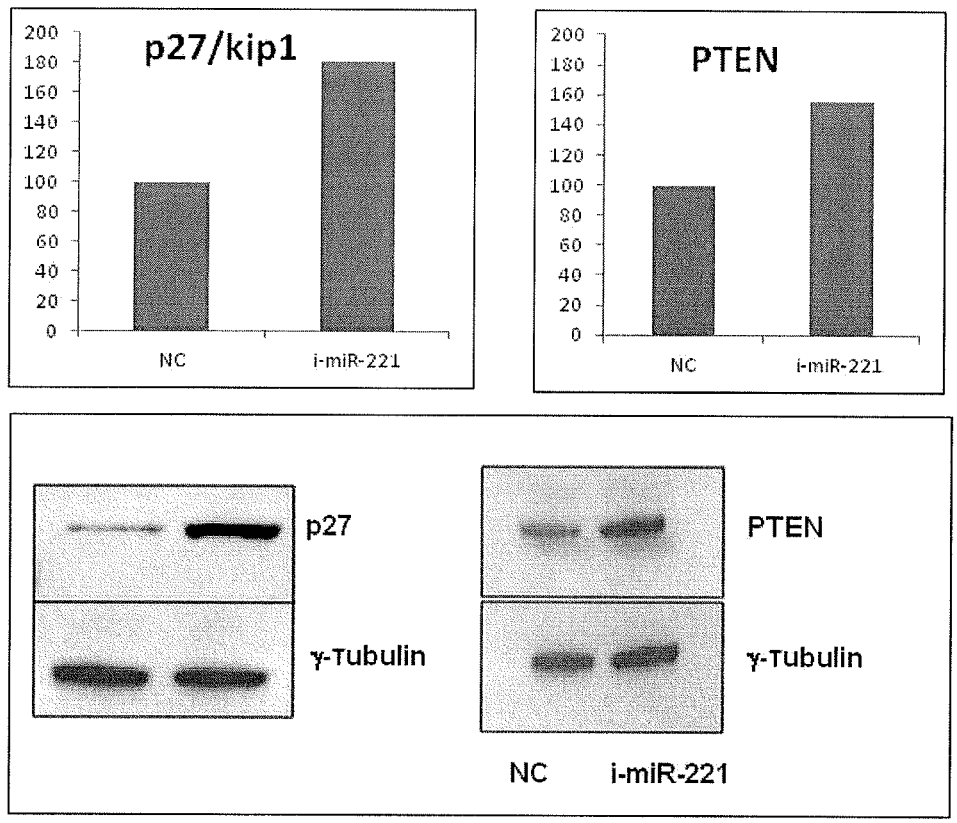
FIGURE 6D
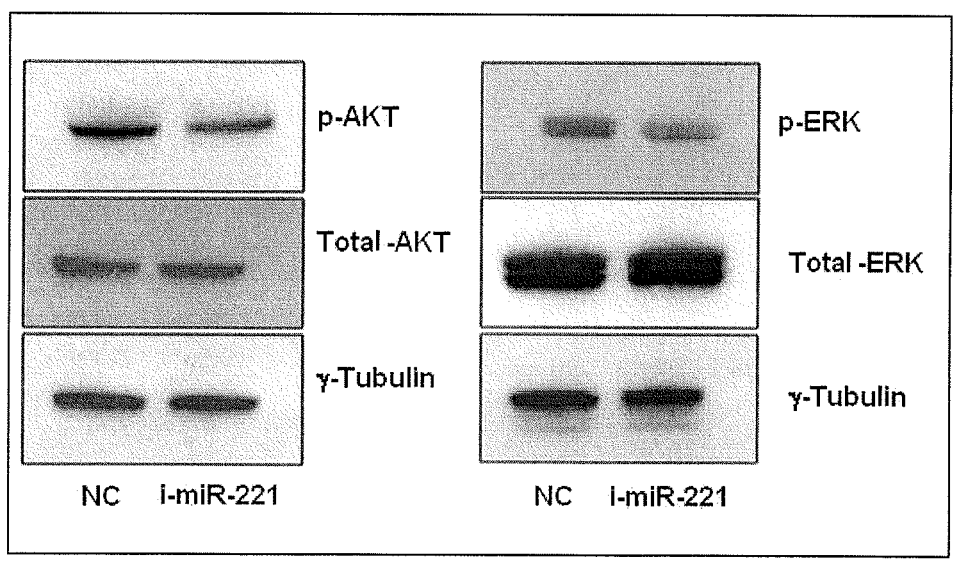
FIGURE 6E

SEQUENCE LISTING

```
<160> NUMBER OF SEQ ID NOS: 3

<210> SEQ ID NO 1
<211> LENGTH: 13
<212> TYPE: DNA
<213> ORGANISM: Artificial Sequence
<220> FEATURE:
```

```
-continued

<223> OTHER INFORMATION: Synthetic
<220> FEATURE:
<221> NAME/KEY: Locked_Nucleic_Acid
<222> LOCATION: (1)..(1)
<220> FEATURE:
<221> NAME/KEY: Phosphorothioate_Bond
<222> LOCATION: (1)..(2)
<220> FEATURE:
<221> NAME/KEY: Phosphorothioate_Bond
<222> LOCATION: (2)..(3)
<220> FEATURE:
<221> NAME/KEY: Phosphorothioate_Bond
<222> LOCATION: (3)..(4)
<220> FEATURE:
<221> NAME/KEY: Locked_Nucleic_Acid
<222> LOCATION: (4)..(4)
<220> FEATURE:
<221> NAME/KEY: Phosphorothioate_Bond
<222> LOCATION: (4)..(5)
<220> FEATURE:
<221> NAME/KEY: Locked_Nucleic_Acid
<222> LOCATION: (5)..(5)
<220> FEATURE:
<221> NAME/KEY: Phosphorothioate_Bond
<222> LOCATION: (5)..(6)
<220> FEATURE:
<221> NAME/KEY: Phosphorothioate_Bond
<222> LOCATION: (6)..(7)
<220> FEATURE:
<221> NAME/KEY: Locked_Nucleic_Acid
<222> LOCATION: (7)..(7)
<220> FEATURE:
<221> NAME/KEY: Phosphorothioate_Bond
<222> LOCATION: (7)..(8)
<220> FEATURE:
<221> NAME/KEY: Phosphorothioate_Bond
<222> LOCATION: (8)..(9)
<220> FEATURE:
<221> NAME/KEY: Locked_Nucleic_Acid
<222> LOCATION: (9)..(9)
<220> FEATURE:
<221> NAME/KEY: Phosphorothioate_Bond
<222> LOCATION: (9)..(10)
<220> FEATURE:
<221> NAME/KEY: Phosphorothioate_Bond
<222> LOCATION: (10)..(11)
<220> FEATURE:
<221> NAME/KEY: Locked_Nucleic_Acid
<222> LOCATION: (11)..(11)
<220> FEATURE:
<221> NAME/KEY: Phosphorothioate_Bond
<222> LOCATION: (11)..(12)
<220> FEATURE:
<221> NAME/KEY: Locked_Nucleic_Acid
<222> LOCATION: (12)..(12)
<220> FEATURE:
<221> NAME/KEY: Phosphorothioate_Bond
<222> LOCATION: (12)..(13)

<400> SEQUENCE: 1
cagacaatgt agc                                                    13

<210> SEQ ID NO 2
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: Phosphorothioate_Bond
<222> LOCATION: (1)..(2)
<220> FEATURE:
<221> NAME/KEY: Locked_Nucleic_Acid
<222> LOCATION: (2)..(2)
<220> FEATURE:
<221> NAME/KEY: Phosphorothioate_Bond
<222> LOCATION: (2)..(3)
```

```
<220> FEATURE:
<221> NAME/KEY: Locked_Nucleic_Acid
<222> LOCATION: (3)..(3)
<220> FEATURE:
<221> NAME/KEY: Phosphorothioate_Bond
<222> LOCATION: (3)..(4)
<220> FEATURE:
<221> NAME/KEY: Locked_Nucleic_Acid
<222> LOCATION: (4)..(4)
<220> FEATURE:
<221> NAME/KEY: Phosphorothioate_Bond
<222> LOCATION: (4)..(5)
<220> FEATURE:
<221> NAME/KEY: Phosphorothioate_Bond
<222> LOCATION: (5)..(6)
<220> FEATURE:
<221> NAME/KEY: Locked_Nucleic_Acid
<222> LOCATION: (6)..(6)
<220> FEATURE:
<221> NAME/KEY: Phosphorothioate_Bond
<222> LOCATION: (6)..(7)
<220> FEATURE:
<221> NAME/KEY: Phosphorothioate_Bond
<222> LOCATION: (7)..(8)
<220> FEATURE:
<221> NAME/KEY: Locked_Nucleic_Acid
<222> LOCATION: (8)..(8)
<220> FEATURE:
<221> NAME/KEY: Phosphorothioate_Bond
<222> LOCATION: (8)..(9)
<220> FEATURE:
<221> NAME/KEY: Locked_Nucleic_Acid
<222> LOCATION: (9)..(9)
<220> FEATURE:
<221> NAME/KEY: Phosphorothioate_Bond
<222> LOCATION: (9)..(10)

<400> SEQUENCE: 2
cagatgtagc                                                          10

<210> SEQ ID NO 3
<211> LENGTH: 13
<212> TYPE: DNA
<213> ORGANISM: Artificial Sequence
<220> FEATURE:
<223> OTHER INFORMATION: Synthetic

<400> SEQUENCE: 3
ctgagaaagt acc                                                      13
```

INHIBITORS OF MIRNAS 221 AND 222 FOR ANTI-TUMOR ACTIVITY IN MULTIPLE MYELOMA

CROSS REFERENCE TO RELATED APPLICATIONS

This application is a continuation of International Patent Application No. PCT/IB2013/050328, filed on Jan. 14, 2013, the contents of which are incorporated by reference herein, in their entirety and for all purposes.

REFERENCE TO A SEQUENCE LISTING

This application includes a Sequence Listing submitted electronically as a text file named MBW12999_PCT_SEQUENCE_LISTING.txt, created on Jan. 13, 2013, with a size of 2,000 bytes. The Sequence Listing is incorporated by reference herein.

TECHNICAL FIELD

The present invention refers to the field of pharmaceuticals and biotechnology. In particular, the present invention refers to inhibitors of miRNAs 221 and 222, and to their use as medicaments in the treatment of multiple myeloma.

BACKGROUND OF THE INVENTION

Multiple myeloma (MM) is a hematologic malignancy characterized by proliferation of neoplastic plasma cells in the bone marrow. Although recent therapeutic options for MM have led to a considerable improvement of patient survival, the course of this disease remains lethal in most of cases. A wide number of complex genetic aberrations contributes to the multistep transformation process of plasma cells within the human bone marrow microenvironment (huBMM), which plays an essential role for growth, survival and the drug resistance of tumor cells. There is now a rising body of evidence demonstrating that these aberrations may affect the microRNAs (miRNA) expression in MM, which in turn translates into aberrant translation of messenger RNA. Therefore, the miRNA network is progressively disclosing its relevant key involvement in the pathogenesis of this important disease.

MicroRNAs are a class of regulatory non-coding RNAs of 19-25 nucleotides in length that act by targeting specific messenger RNAs (mRNAs) for degradation or inhibition of translation through base pairing to partially or fully complementary sites. At present, the miRNA network, which includes several hundreds of sequences, is involved in a variety of normal biological functions as well as in tumorigenic events, since deregulated miRNAs can act as oncogenes (Onco-miRNAs) or tumor-suppressors (TS-miRNAs). Changes in gene copy number, chromosomal translocation, mutations, transcriptional activation, epigenetic silencing and defective miRNA development are variably responsible of this deregulation. Therefore, miRNAs are emerging as new potential multi-target agents, due to their ability to target multiple genes, in the context of signaling networks involved in cancer promotion or repression.

Among miRNAs significantly deregulated in human cancer, miR-221 and miR-222 are of great interest for potential clinical applications. MiR-221 and miR-222 are highly homologous microRNAs encoded in tandem on the X chromosome, whose up-regulation has been recently described in several types of human tumors. MiR-221 and miR-222 act as oncogenic miRNAs that facilitate cell proliferation via down-regulation of p27 and/or p57, which negatively regulate the cell cycle progression from G1 to S phase.

Several reports suggested a key role of miR-221/222 in tumorigenesis. For example, Garofalo et al. have recently shown that up-regulation of miR-221/222 expression, by targeting PTEN and TIMP3, confers resistance to TRAIL-induced cell death and enhances tumorigenicity of lung and liver cancer cells. Chun-Zi et al. demonstrated that miR-221 and miR-222 by modulation of PTEN expression regulate radiosensitivity, cell growth and invasion of gastric cells. More recently, Pineau et al. showed that the treatment with LNA-modified miR-221 inhibitors reduced the growth of liver cancer cells that overexpressed miR-221/222 by targeting a DNA damage-inducible transcript 4 (DDIT4), a modulator of the mTOR pathway. In addition, Galardi et al. showed that the treatment with miR-221/222 antisense oligonucleotides reduces tumor growth by increasing intratumoral p27kip1 amounts.

Taken together, all these evidences support the notion that silencing miR-221/222 may represent a valuable anti-tumor option.

However, the variability of the molecular profile of human tumors does not allow transferring the experimental findings in a tumor system to further different tumor systems. Therefore, even if the above experiments and considerations may suggest the general idea of an anti-tumor activity of miR-221/222 inhibitors, said activity cannot be predicted or expected for tumors for which evidence has never been provided in widely recognized experimental models. Assessing the role of a miRNA in a tumor model requires a long and difficult scientific investigation based on the genetic and molecular mechanism of a specific tumor and this kind of investigation is also affected by dead end findings, thorough reconsideration and starting of new experimental designs.

WO2006108718 discloses the use of miRNA 221 and 222 for the treatment of GIST (gastrointestinal stromal tumor), kit-dependent acute leukemias, erythroleukemia, papillary thyroid carcinoma, or other kit-dependent tumors or disease conditions, and the use of inhibitors of said miRNAs in therapy for suppressed hematopoiesis in cancer patients, β-thalassemia, and other β-hemoglobin diseases. Multiple myeloma is not mentioned and it does not fall within any of the mentioned pathological conditions; in particular, it is not regarded as a c-kit-driven or c-kit-dependent tumor.

WO2011068546 discloses a diagnostic or prognostic indicator of multiple myeloma that comprises a global expression profile of total miRNAs in the subject with a pattern of 39 up-regulated and 1 down-regulated gene. MiRNA 222 is one of the 39 up-regulated miRNAs. However, the document only refers to a diagnostic or prognostic use of the miRNA pattern, no mention is made to the use of the individual miRNAs or their inhibitors in the treatment of multiple myeloma. In fact, a method for treating a subject having multiple myeloma is suggested but it relies on the administration to the patient of one or more therapeutic compounds that inhibits miRNA maturation pathway, in particular by inhibiting expression of one or both of AGO2 or DICER1 genes at the nucleic acid or protein level, by means of a shRNA, an antibody or other small molecule inhibitor. Therefore, it does refer to a whole miRNA blockade but does not refer to the inhibition of an individual miRNA among the 39 upregulated miRNAs. This approach produces a completely different profile of toxicity, which cannot be correlated with or compared to the profile obtainable with individual miRNA inhibition. The diagnostic method also relates to the global expression profile and not to the analysis of individual miRNAs. In table 5, expression of individual miRNAs is studied and associated with GEP-defined risk score and proliferation index. However, specific target are not identified and, in any case, mir-222 is not mentioned at all in the table. Besides, it is suggested that some individual miRNAs alone cannot significantly contribute to disease progression, while only their synergy might significantly contribute to MM disease progression. Therefore, there is no suggestion that the targeting of individual miRNA could be effective. Furthermore, in the experiment showing that higher total expression levels of some miRNAs might be associated with multiple myeloma disease initiation, the miRNAs used in the experiment were randomly selected; the identification of target miRNAs would therefore have required an undue burden of experimentation for the skilled in the art.

WO2012080721 discloses novel biological markers for plasma cell disorders, such as multiple myeloma, and in particular, it relates to the use of microRNAs, as diagnostic and prognostic markers in assays for detecting such disorders. Among the disclosed miRNAs, miR-221 is also disclosed but miR-16 is presented as the most significant since it is particularly highly expressed. As for the above document, no mention is made to the possible use of the disclosed miRNAs as a target in the treatment of said disorders. In fact, once a diagnosis of myeloma is made by detecting a set of miRNAs, the patients will undergo conventional therapy based on cyclophosphamide, thalidomide and dexamethasone.

US20100298410 discloses oligonucleotides, which target and inhibit in vivo certain microRNAs, among which miR-221 and miR-222 are also disclosed in a list. The document also generally provides for a method for the treatment of a disease associated with the presence or overexpression of the microRNAs. With regard to miR-221 and miR-222, the only therapeutic indications disclosed are prostate carcinoma, human thyroid papillary carcinoma and human hepatocellular carcinoma. Multiple myeloma is only mentioned in a list of cancers, which may be treated by the oligonucleotides of the invention. Said claimed oligomers are 7-10 nucleotides in length; in particular, the oligomer used for the inhibition of miR-221 and miR-222 is a 7-mer LNA-antimiR. Direct evidence of anti-myeloma activity of the disclosed oligomers is not provided in the application, and it cannot be inferred from experimental evidences of anti-tumor activity in other cancer systems, as already explained above.

The role of miR-221/222 in myeloma has been mentioned in the paper of Lionetti et al. (2009) (7), where the expression profiles of a series of miRNAs in a set of 38 MM patients have been studied. Said MM patients have been classified according to the TC (Translocation/Cyclin) classification which is based on the presence of the recurrent IGH (immunoglobulin heavy chain) chromosomal translocations and cyclins D expression: TC1: patients characterized by the t(11;14) or t(6;14) translocation; TC2: patients showing low to moderate levels of the CCND1 gene in the absence of any primary IGH translocation; TC3: patients that do not fall into any of the other groups; TC4: patients showing high CCND2 levels and the presence of the t(4;14) translocation; TC5: patients with either the t(14;16) or the t(14;20) translocation (Hideshima et al., Blood 2004). MiR-221/222 have been found to be deregulated in MM with significant up-regulation in a subset of patients classified as TC2, showing low to moderate levels of the CCND1 gene in the absence of any primary IGH translocation, and TC4, that shows t(4;14) translocation. However, a potential anti-tumor effect of any in vitro or in vivo perturbation of miR-221/222 is not addressed nor even mentioned in this document.

Therefore, there is still the need of an effective tool for the therapy of multiple myeloma.

In particular, multiple myeloma is a general disease comprising different disease subsets. This represents a relevant issue for the efficacy of treatment. In fact, different subtypes of patients can be identified, as according to the TC classification above disclosed, and different treatments may therefore be required. The specific target of patients with higher potential of benefit from miRNA inhibitor treatment would thus represent an extremely important advantage since it would avoid potential toxicity for non-responding patients, as well as costs for ineffective treatment. Within the general problem of the lack of an efficient tool for therapy of multiple myeloma, a more specific problem of efficiently targeting specific subset of patients can therefore be identified.

Another problem is the provision of an inhibitor of miR-221 and miR-222 able of inhibiting the two of them at the same time, thus providing an immediate therapeutical advantage.

Still another problem is to provide selective miRNA inhibitors.

A further problem is to provide inhibitors stable when administered in a subject.

It has now been found that silencing miR-221 and miR-222 with anti-miR-221 and/or anti-miR-222 exerts a powerful anti-tumor activity in vitro in MM cells and mostly evident in clinically relevant xenograft models of human MM. These models are recognized for starting a clinical development for the therapy of multiple myeloma.

Also, since miR-221 and miR-222 are particularly overexpressed in some MM subtypes (TC2 and TC4) their specific targeting represents a strong tool for rational patient selection and treatment.

The inhibition of miR transcriptional regulation requires the overcoming of several challenges.

In particular, an efficient miR inhibitor should have high binding affinity and nuclease resistance and be efficient for in vivo delivery. Different chemically modified oligonucleotides including 2'-O-methyl, locked nucleic acid (LNA) or 3' cholesterol-conjugated with full o partial phosphorothioate backbone, have been proposed to silence miRs in vivo. In addition, tiny LNAs, fully LNA-modified phosphorothioate oligonucleotides, designed with perfect complementary miRs seed sequence, have been disclosed as valid miRs knockdown in different tumor model in vivo.

LNA miRNA-inhibitors commercially available have been used for the purposes of the present invention.

Further, novel miR-221 and miR-222 inhibitors (LNA-i-miR-221 and LNA-i-miR-222) able to antagonize miR-221 and miR-222 activity in vitro and in vivo have been designed in order to provide a more effective tool for the inhibition of said miRNAs.

Advantageously, these novel inhibitors are endowed with enhanced stability, allowing a better therapeutical efficacy.

SUMMARY OF THE INVENTION

Inhibitors of miR-221 and miR-222 for use in the treatment of multiple myeloma are an object of the present invention.

Commercially available inhibitors of miR-221 and 222 are suitable for the purpose of the present invention. For example, those provided by Ambion (Life Technologies).

The present invention also provides novel inhibitors of miR-221 and miR-222. In the foregoing, the novel inhibitors are called LNA-i-miR-221 and LNA-i-miR-222, which are also specific objects of the present invention.

Said novel inhibitors can inhibit both miR-221 and miR-222 due to the partially shared functionally relevant sequence.

Said novel LNA-inhibitors have enhanced selectivity and efficiency in the inhibitory activity on the target sequences and at the same time show a remarkable improvement in stability, thus allowing its systemic delivery. This advantage of the novel inhibitors of the present invention is of major relevance since it makes them suitable for clinical application, where intravenous administration is the conventional route.

In particular, LNA-i-miR-221 and LNA-i-miR-222 for use in the treatment of multiple myeloma are an object of the present invention.

The use of said inhibitors provides the advantages of a successful delivery and a powerful anti-tumor activity, thus improving patient outcome in MM patients. In particular, said use is particularly effective in TC2 and TC4 patient subsets.

In a particular embodiment, the treatment of multiple myeloma with an inhibitor of miR-221 and miR-222, in particular with LNA-i-miR-221 and LNA-i-miR-222, is carried out on a subset of multiple myeloma patients selected from the group consisting of TC2 and TC4 patient subsets.

The present invention thus provides to the medical doctor the advantage of treatment personalization.

Means of delivery of said inhibitors are also within the scope of the present invention.

In particular, the inhibitors can be administered in saline solution or included in lipidic nanovectors. The inhibitors according to the present invention can also be administered by any conventional vector and formulation.

(A) SAM multi-class analysis of differential expression of miR-221 and miR-222 in TC classified MM samples (N=normal). Significant higher miR-221/222 expression in TC2 and TC4 patient groups, (q-value=0) is shown.

(B) Differential expression of miR-221 and miR-222 in 16 MM cell lines by Affymetrix GeneChip® miRNA array. Histogram bars indicate miR-221 or miR-222 expression values normalized by miRNA QC Tool (Affymetrix).

Figure 2:
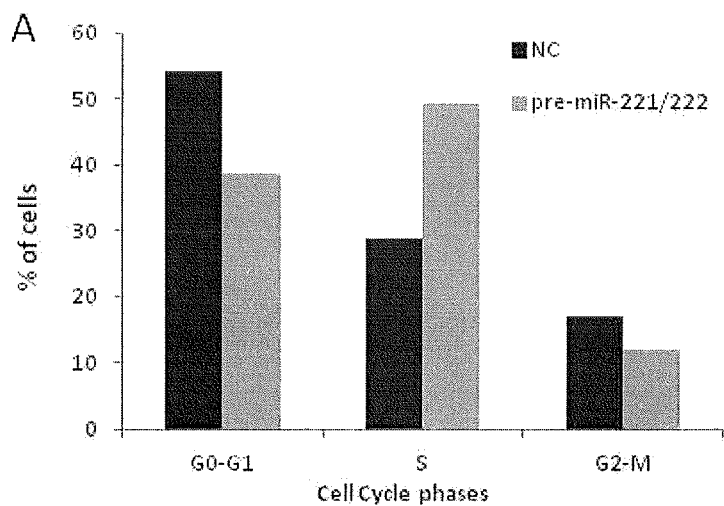
Figure 2:
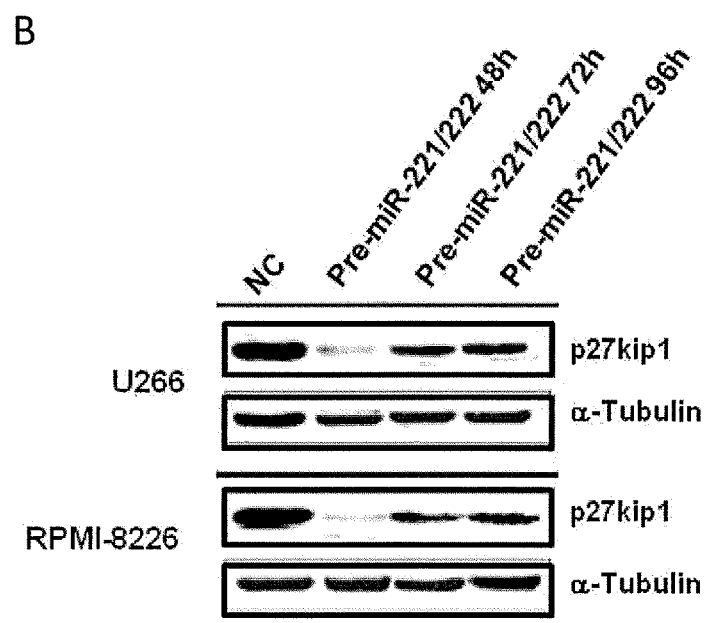

FIG. 2 shows the molecular effects induced by transient expression of miR-221/222 in MM cell lines.

A) Cell cycle analysis in pre-miR-221/222 transfected U266 cells revealed increase in the percentage of cells in S phase.

B) Western blot (WB) analysis of p27kip1 protein in pre-miR-221/222 transfected U266 and RPMI-8226 cells showed reduction of p27kip1 protein. α-tubulin was used as control.

Figure 3A:
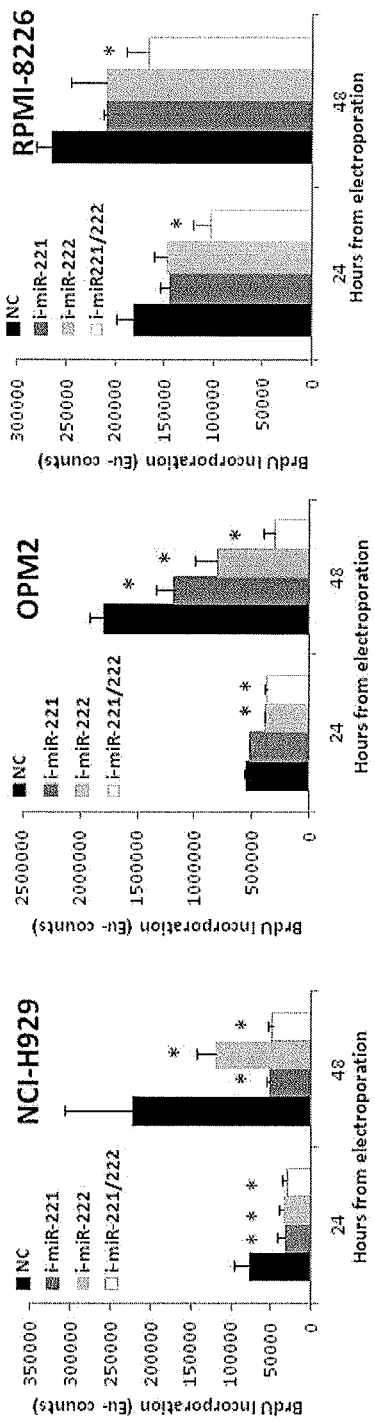

FIGS. 3A through 3E show miR-221/222 inhibitors downregulate miR-221/222 expression and exert anti-proliferative activity in myeloma cell lines. The specificity of their activity is demonstrated by up-regulation of proteins, which are known as selective targets of miR-221/222:

In FIG. 3A, BrdU incorporation after transfection of synthetic miR-221 or miR-222 or miR-221/222 inhibitors or NC (negative controls) in NCI-H929, OPM2 and RPMI-8226 cells, 24 and 48 hours after transfection. Averaged values of three independent experiments are plotted including ±SD. P-values were calculated by Student's t test, two-tailed (*P<0.05).

In FIG. 3B, q-RT-PCR of miR-221 and miR-222 after transfection with miR-221 or miR-222 inhibitors (i-miR-221/222) and NC in OPM2 cells. The results are shown as average miRNA expression after normalization with RNU44 and ΔΔCt calculations. Data represent the average of 3 independent experiments ±SD.

In FIG. 3C, q-RT-PCR of p27kip1, PUMA, PTEN and p57kip2 after transfection with i-miR-221/222 or NC in OPM2 cells. The results are shown as average mRNA expression after normalization with GAPDH and ΔΔCt calculations. Data represent the average of 3 independent experiments ±SD.

In FIGS. 3D and 3E, Western blotting of p27/kip1 and PTEN protein in OPM2 cells 24 and 48 hours after transfection with i-miR-221/222 and NC. The protein loading control was performed using γ-Tubulin. Experiments were performed in triplicates. MiR-221/222 inhibitory effects on protein levels reached in all points statistical significance (P<0.05).

Figure 4A:
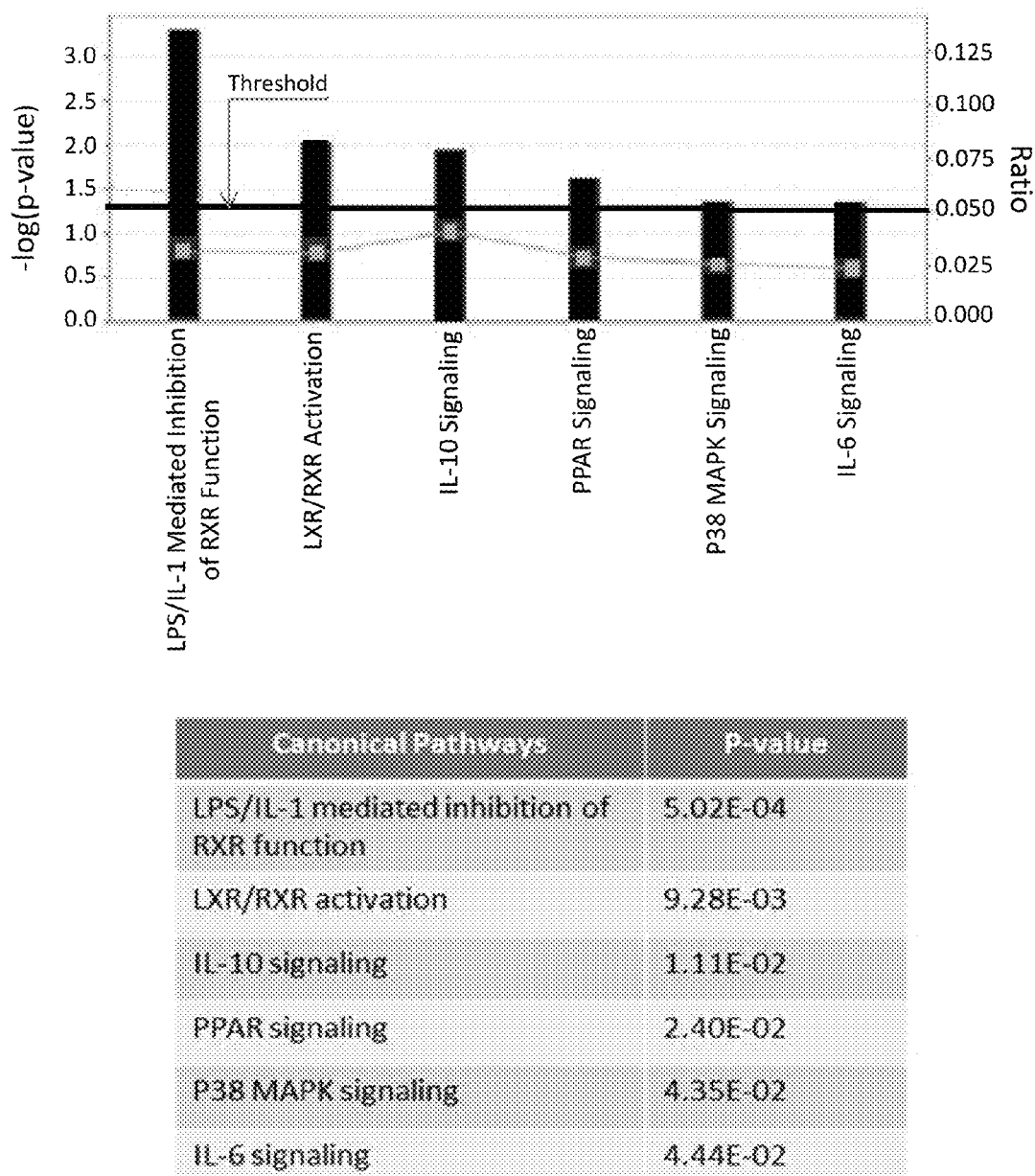
Figure 4B:
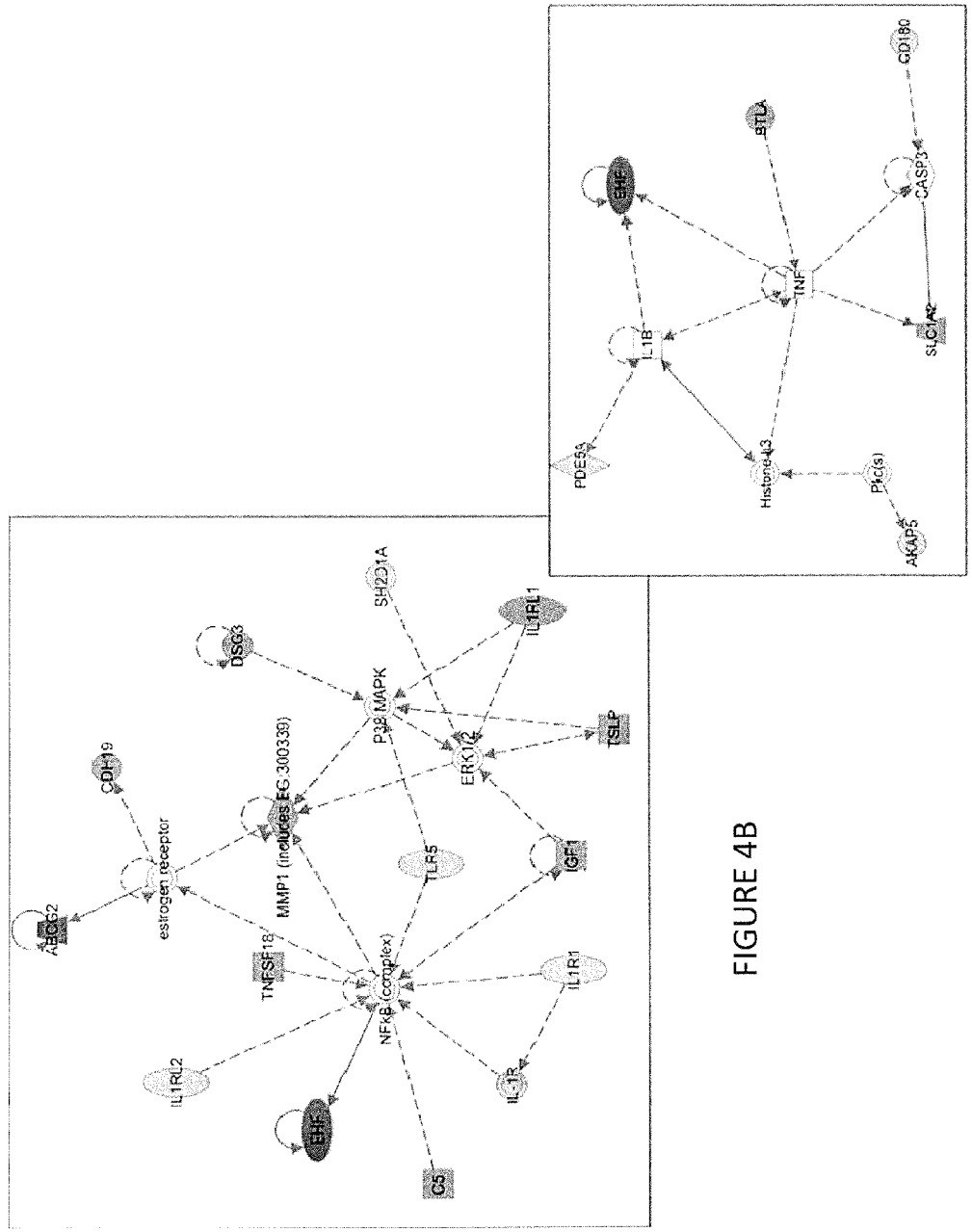

FIGS. 4A and 4B show gene expression profile analysis after miR-221/222 knockdown in MM cells. MiR-221/222 inhibitors induce strong perturbation of overall gene expression profiles of multiple myeloma cells. Pathway analysis demonstrated that signaling related to proliferation and survival are mostly affected by miR-221/222 inhibitors.

FIG. 4A) Gene expression profile of OPM2 cells transfected with 100 nmol/l miR221/222 inhibitors after 24 h and analyzed using the Gene 1.0 ST array chip. Assays were performed in triplicate. Functional categories of pathways modulated by i-miR221/222 are illustrated. All genes significantly modulated (fold change>1.5) were subjected to Ingenuity Pathway Analysis (IPA). The bar graphs show pathways most modulated, based on significance (P-value and ratio).

FIG. 4B) Pathways with higher scores have been used to form a composite network representing the underlying biology of the effect. The panel shows the principal nodes in the networks modulated. Continuous and discontinuous lines represent direct and indirect functional and physical interaction between genes demonstrated in literature.

Figure 5A:
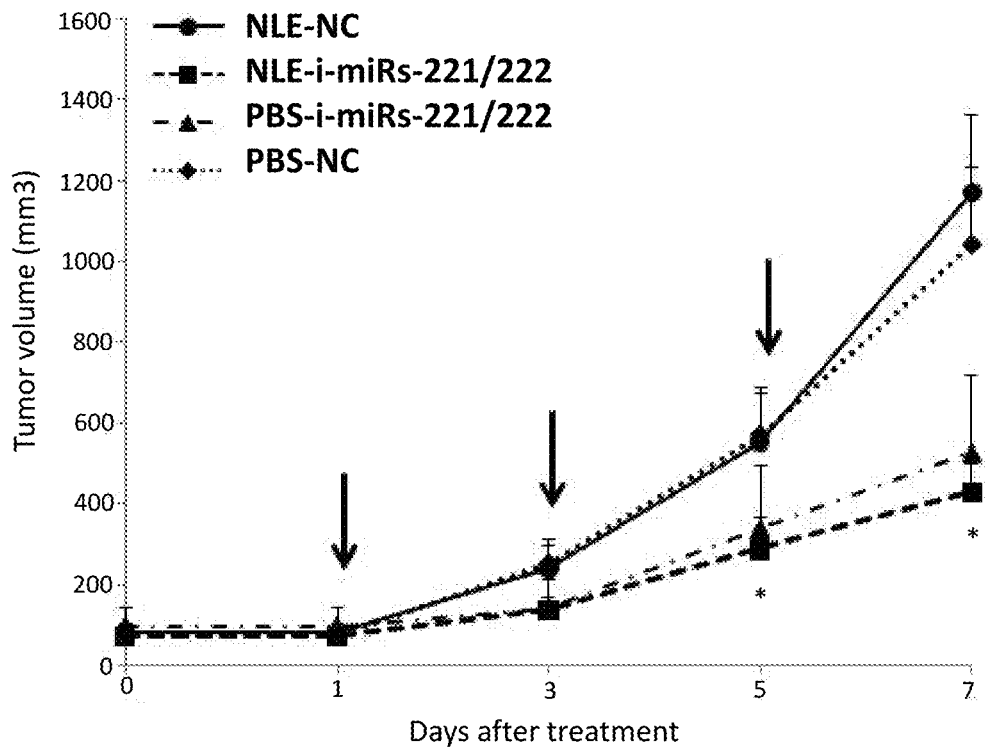
Figure 5B:
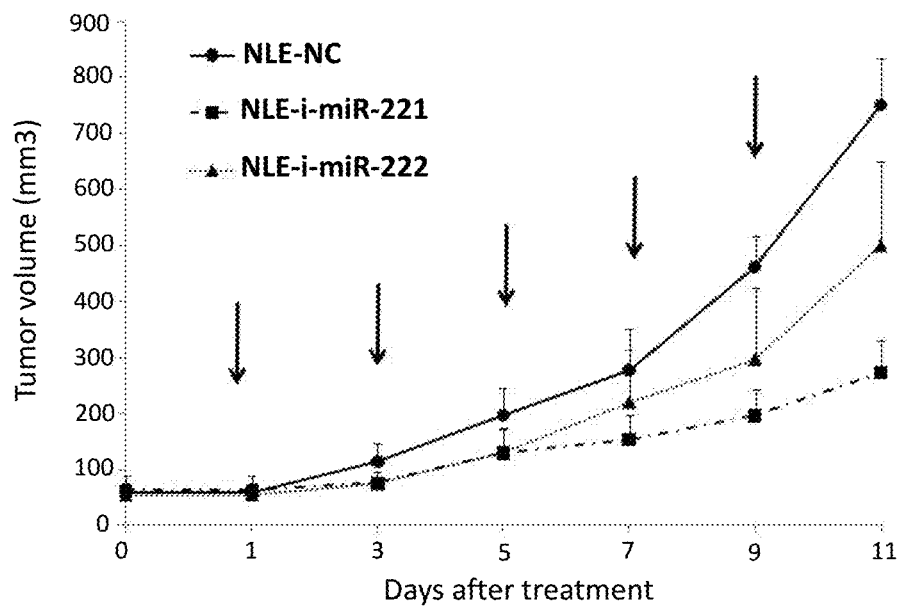
Figure 5C:
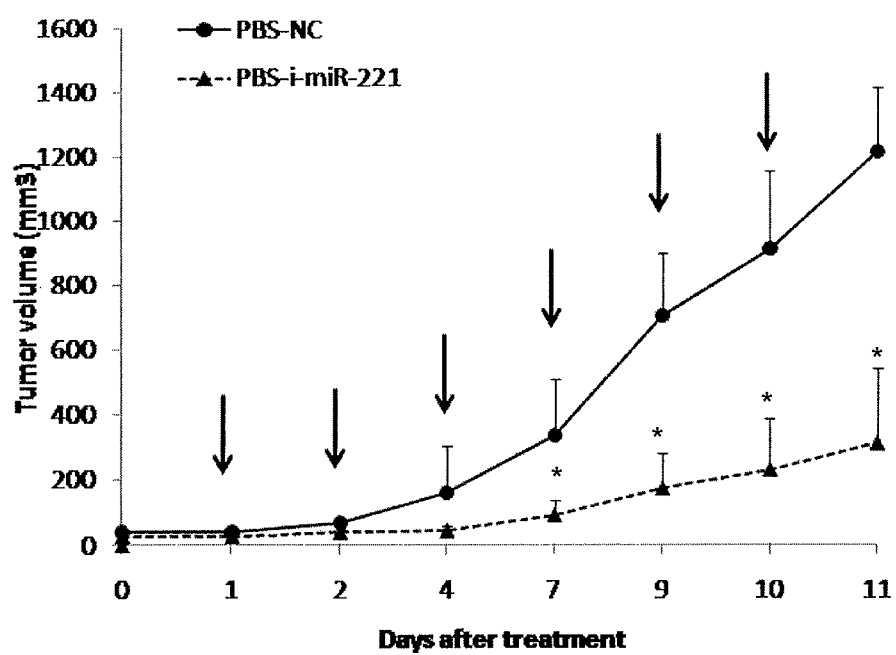

FIGS. 5A through 5C show in vivo treatment with miR-221/222 inhibitor of immunodepressed mice, which have been xenografted with multiple myeloma cells. Results show a tumor growth inhibition thus clearly demonstrating the anti-tumor activity of the inhibitors in a validated experimental model:

In FIG. 5A, Effects of formulated (NLE) and unformulated (PBS) miR-221/222 inhibitors (i-miR-221/222) in OPM2 xenografts by intratumoral injections. Palpable subcutaneous tumor xenografts were repeatedly treated every 2 days, as indicated by arrows, with 20 μg of NLE-i-miR-221/222, or scrambled oligonucleotide (NLE-NC) or PBS-i-miR221/222 or PBS-NC. Tumors were measured with an electronic caliper every 2 days, averaged tumor volume of each group and ±SD are shown. P values were calculated of i-miR-221/222 versus NC (Student's t test, two-tailed). (*) indicate significant P-values (P<0.05). Number of 5 animals are included in each group.

In FIG. 5B, Effects of formulated miR-221 or miR-222 inhibitors in OPM2 xenografts by intratumoral injections. Palpable subcutaneous tumor xenografts were repeatedly treated every 2 days, as indicated by arrows, with 20 μg of NLE-i-miR-221 or NLE-i-miR-222, or NLE-NC. Tumors were measured with an electronic caliper every 2 days, averaged tumor volume of each group and ±SD are shown. P values were calculated of miRNAs inhibitors versus NC (Student's t test, two-tailed). (*) indicate significant P-values (P<0.05). Number of 5 animals are included in each group.

In FIG. 5C, Effects of buffer phosphate miR-221 inhibitors (PBS-i-miR-221) or scrambled control (PBS-NC) in OPM2 xenografts by intratumoral injections. Palpable subcutaneous tumor xenografts were repeatedly treated every 2 days, as indicated by arrows, with 20 µg of PBS-i-miR-221, or NC. Tumors were measured with an electronic caliper every 2 days, averaged tumor volume of each group and ±SD are shown. P values were calculated of PBS-i-miR-221 averaged tumor volume versus NC (Student's t test, two-tailed). (*) indicate significant P-values (P<0.05). Number of 5 animals were included in each group.

Figure 6A:
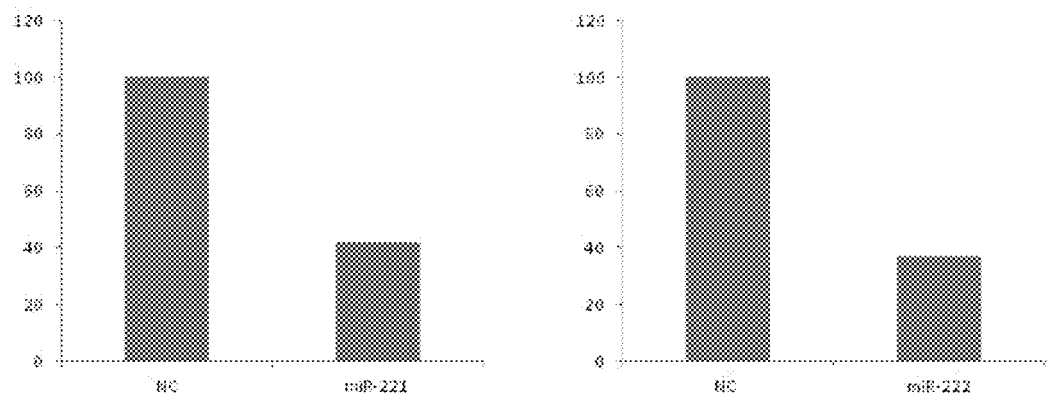

FIGS. 6A through 6E show miR-221 inhibitors activity and targets silencing in MM mouse model. MiR-221 inhibitors specificity of anti-tumor effect is demonstrated by selective down-regulation in the tumor tissue of miR-221 and miR-222 and up-regulation of their validated targets:

In FIG. 6A, q-RT-PCR of miR-221 and miR-222 in retrieved tumors from animal treated with i-miR-221 or NC. The results are shown as average miRNA expression after normalization with RNU44 and ΔΔCt calculations. Data represent the average of 3 independent experiments ±SD.

Figure 6B:
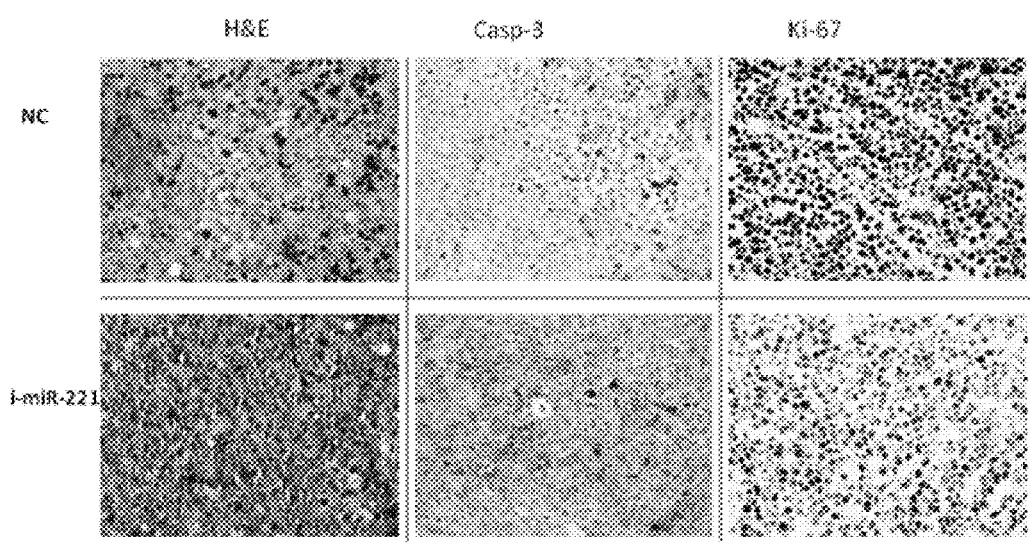

In FIG. 6B, Xenograft tumors retrieved from mice at the end of treatment with i-miR221 or NC. Histologies (H&E, 20-fold magnification) and Caspase-3 and Ki-67 immunohistochemical (40-fold magnification) staining of OPM2 tumors are shown.

In FIG. 6C, p27kip1 and PTEN expression levels by q-RT-PCR of total RNA extracted from OPM2 tumors treated with PBS-i-miR-221 or NC after mice sacrifice. Raw Ct values were normalized to GAPDH housekeeping mRNA and expressed as ΔΔCt values calculated using the comparative cross threshold method. Values represent mean observed in 3 different experiment ±SD.

In FIG. 6D, Western blot analysis of p27kip1 and PTEN protein in retrieved tumors from mice treated with PBS-i-miR-221or NC. The protein loading control was γ-Tubulin. Experiments were performed in triplicates. PBS-i-miR-221 effects on protein levels reached in all points statistical significance (P<0.05).

In FIG. 6E, Western blot analysis of total AKT and p-AKT protein levels (left panel) and total ERK and p-ERK protein levels (right panel) in retrieved OPM2 tumors from mice treated with PBS-i-miR-221 or NC. The protein loading control was γ-Tubulin. Experiments were performed in triplicates. PBS-i-miR-221 inhibitor effects on protein levels reached in all points statistical significance (P<0.05).

Figure 7A:
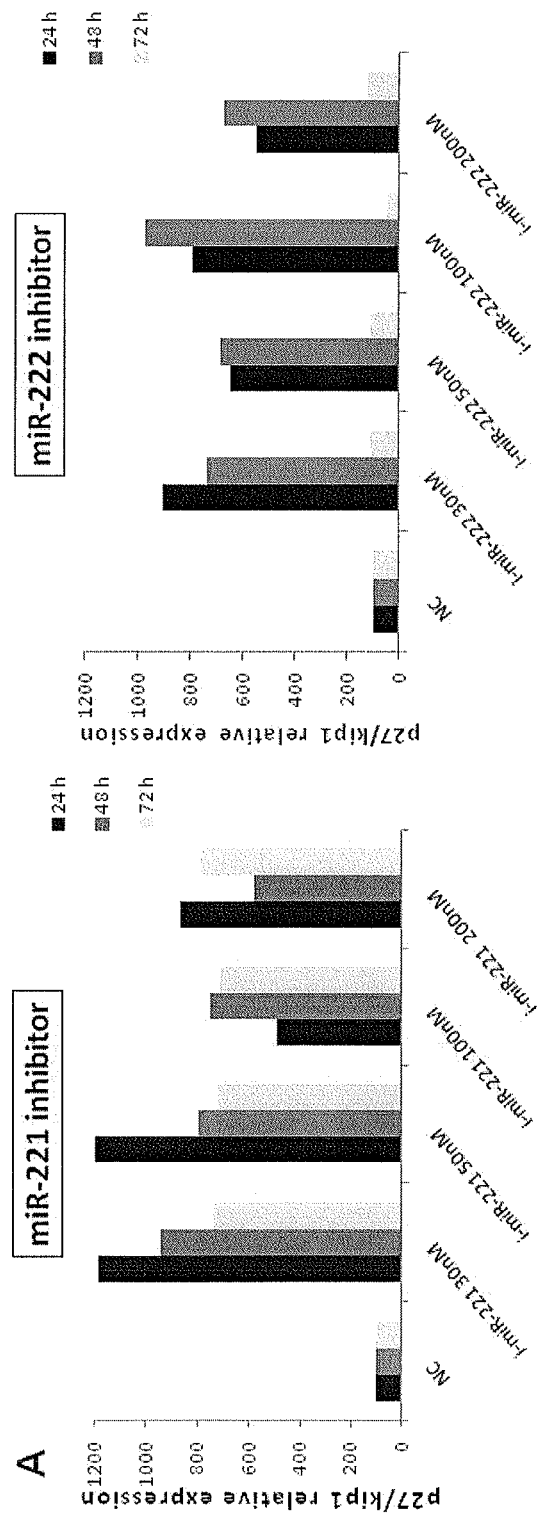
Figure 7B:
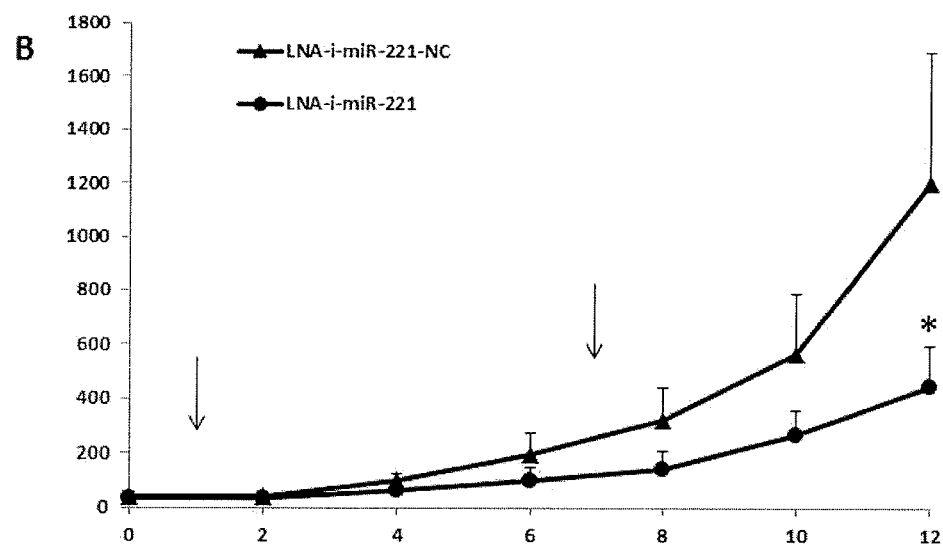

FIGS. 7A and 7B show the strong anti-tumor activity in vitro and in vivo of novel LNA-i-miR-221, an enhanced synthetic miR-221/222 inhibitor:

In FIG. 7A, Molecular effects induced by transient inhibition of miR-221/222 in MM cells.

q-RT-PCR of p27kip1 after OPM2 transfection with increasing concentrations of LNA-i-miR-221 or LNA-i-miR-222. NC was used as above. The results are shown as average mRNA expression after normalization with GAPDH and ΔΔCt calculations. Data represent the average of 3 independent experiments ±SD.

In FIG. 7B, Systemic treatment with LNA-i-miR-221 compound inhibits MM growth in vivo. Tumor growth inhibition of LNA-i-miR-221 compound (i-miR-221/222) in OPM2 xenografts by intraperitoneal injections is shown. When subcutaneous tumor xenografts became palpable six animals for each group were repeatedly treated as indicated by arrows, with LNA-i-miR-221 or specific miR-221 scrambled inhibitors (LNA-i-miR-221-NC). Tumors were measured with an electronic caliper every 3 days, averaged tumor volume of each group and ±SD are shown. P-values were calculated of LNA-i-miR-221 versus LNA-i-miR-221-NC (Student's t test, two-tailed). (*) indicate significant P-values (P<0.05).

DESCRIPTION OF THE INVENTION

Within the context of the present invention, the term "microRNA" or "miRNA" means a short ribonucleic acid (RNA) molecule found in eukaryotic cells.

Within the context of the present invention, the terms "anti-miR", "miRNA inhibitor" and "i-miR" are synonymous, and they all refer to molecules which bind and inhibit one or more specific miRNAs.

Within the context of the present invention, the term "Locked Nucleic Acid" or "LNA" refers to a nucleotide with the ribose ring locked in an N-type conformation by a 2'-O, 4'-C methylene bridge. LNA units are described in inter alia WO 99/14226, WO 00/56746, WO 00/56748, WO 01/25248, WO 02/28875, WO 03/006475 and WO 03/095467 and references cited therein.

Within the context of the present invention, a PS-oligonucleotide is an oligonucleotide with a phosphorothioate bond, where a phosphorothioate bond is the substitution with a sulfur atom of a non-bridging oxygen in the phosphate backbone of said oligonucleotide.

Within the context of the present invention, multiple myeloma is a cancer of plasma cells characterized by abnormal proliferation of neoplastic plasma cells in the bone marrow.

The sequences of miR-221 and miR-222 are available in the state of the art with the IDs hsa-miR-221 and hsa-miR-222 (www.microrna.org).

The inhibitors of miR-221 and miR-222 used in the examples 3-5 of the present invention are purchased from Ambion (Life Technologies) and are commercially available. For in vitro experiments, miRNA inhibitors from the family of Anti-miR™ were used. Said inhibitors are single-stranded chemically modified oligonucleotides with a sequence complementary to the miR-221 or miR-222 mature sequences. For in vivo experiments, inhibitors from the family of mirVana™ inhibitors were used. Said inhibitors are small, chemically modified single-stranded RNA molecules designed to specifically bind to and inhibit endogenous miRNA molecules.

Said inhibitors for use in the treatment of multiple myeloma are within the scope of the present invention.

In order to develop enhanced inhibitors more suitable for clinical application, a LNA-phosphorothioate miR-221-3p inhibitor has been designed. It has shown to efficiently antagonize miR-221 activity in vitro and in vivo in t(4;14) multiple myeloma models. The sequence of said 13-mer oligonucleotide inhibitor is: 5'-CAGACAATGTAGC-3' (SEQ ID NO: 1), which is complementary to the nucleotides 66-78 of the miR-221 stem loop, i.e. the secondary structure sequence.

The sequence of the novel miR-221/222 LNA-inhibitor named LNA-i-miR-221, which is an object of the present invention, is: +C*A*G*+A*+C*A*+A*T*+G*T*+A*+G*C, where letters with symbol "+" indicate the positions of LNA and symbol "*" indicates phosphorothioate bonds.

Moreover, a 10-mer miR-222-3p inhibitor was designed with the following sequence 5'-CAGATGTAGC-3' (SEQ ID NO: 2) complementary to the nucleotides 70-79 of the miR-222 stem loop sequence. This short inhibitor includes 7 nucleotides of the 8-mer seed sequence shared between the miR221/222 cluster.

The complete sequence of this novel miR-221/222 LNA-inhibitor, named LNA-i-miR-222, is C*+A*+G*+A*T*+

G*T*+A*+G*C, where letters with symbol "+" indicate the positions of LNA and symbol "*" indicates phosphorothioate bonds.

The advantage of the novel inhibitors of the present invention is that they are able of inhibiting both miR-221 and miR-222 thanks to the sharing of a seed sequence.

They can be used, according to the present invention, either singularly or in combination.

The LNA—oligonucleotides exhibit thermal stability when hybridized to the complementary miRNA strand. In fact the melting temperature (TM) increases 2-8° C. for each incorporated LNA-monomer. The predicted TM for LNA-i-miR-221 is 84° C.

The PS-oligonucleotides are introduced at the 5' end of the oligo to inhibit exonuclease degradation and internally to limit attack by endonucleases.

Modifications of the backbone of the inhibitors of the present invention, which do not substantially affect their activity, are also in the scope of the invention.

The specific structure of said LNA-inhibitor provides for an enhancement of the selectivity and efficiency of the inhibitory activity on the target sequences and at the same time for a remarkable improvement of the stability of the inhibitor. This enhanced stability allows for the systemic delivery of said inhibitors. This advantage of the novel inhibitors of the present invention is of major relevance since it makes them suitable for clinical application, where intravenous administration is the conventional route.

One of the advantages of the use of the inhibitors of the present invention is, therefore, that both unformulated or lipid-based formulated miR-221/222 inhibitors can be successfully delivered, thus the unformulated anti-miR-221/222 has an optimal bioavailability. This can avoid the need of delivery systems for a therapeutic purpose. A more favorable pharmacokinetics may however be achieved by delivery systems like the neutral lipid emulsion (NLE).

The single-strand oligonucleotides miRNA inhibitors of the present invention have a high stability due to chemical stabilization of miRNA sequences. This high stability allows overcoming many potential pharmacokinetic and pharmacodynamic issues related to the use of delivery systems. In particular, the balance between in-targets and off-target effects, which is of course the effectiveness/toxicity balance, is remarkably improved. This is clearly of particular relevance for the use of the inhibitors in clinical practice.

The down-regulation of canonical target by miR-221/222 inhibitors in tumors excised from treated animals further confirms the successful tumor-uptake of miRNA inhibitors at concentration sufficient to give up-regulation of target mRNAs and proteins, which in turn translate in anti-tumor activities.

Therefore, the inhibitors of the present invention provide the advantages of exercising an effective anti-tumor activity in multiple myeloma when systemically administered.

The CDK inhibitor p27 is an important target of miR-221/miR-222, the major player in cell cycle control, which has relevant consequences on the proliferation rate and the cell cycle phase distribution in a variety of human malignancies, including pancreatic cancer, glioblastomas, in thyroid carcinomas, in breast cancer, hepatocellular carcinoma, and lung cancer. We have found that MM cells after miR-221/222 transfection increase for about 20% their S-phase that conversely decreases after miR-221/222 inhibitors treatment.

A further important oncosuppressor gene target identified is the p57kip2 that is reported as miR-221 direct target in the liver where is involved, with an oncogenic function, in hepato-carcinogenesis. In our in vitro experiments we have found that both CDK inhibitors, p27kip1 and p57kip2, are upregulated after miR-221/222 inhibitors treatment, suggesting that these molecules are the major players in cell cycle regulation and proliferation inhibition in MM cells.

Among the most important miR-221/222 gene targets, the tumor suppressor PTEN is known to negatively regulate glioma cell migration. PTEN functions as tumor suppressor by negatively regulating AKT/PKB signaling pathway that in turn inhibit cell cycle progression by p27kip1 inhibition. We have found that in MM cells the PTEN mRNA level increases after miR221/222 inhibitors transfections. Therefore, the major anti-proliferative effect of said inhibitors could be mediated by cell cycle regulation. In fact, we did not detect perturbation in other biological mechanism, as apoptosis, in in vitro experimental setting. The detected low modulation of BBC3/PUMA mRNA, a p53 modulator of apoptosis, supports our hypothesis. The in vivo immunochemistry analysis of apoptosis in i-miR-221 treated tumors has shown the activation of caspase-3 suggesting that other players trigger the apoptotic cascade in in vivo experimental setting.

In view of the above, we have found that the inhibition of a single miRNA, that is able to modulate different genes involved in the same network, acts as a strong inhibitor of the entire cellular pathway. Therefore, the inhibition of miR-221 and miR-222 in multiple myeloma through the inhibitors of the present invention has a greater therapeutic potential respect to the inhibition of a single gene.

Also, genome wide mRNA expression after miR-221/222 knockdown identifies modulation in canonical pathways transducing cell proliferation signals and involving immune response.

The inhibitors of miR-221 and miR-222 are able to inhibit tumor growth both in vitro and in vivo in MM models.

The present invention provides therefore the inhibitors of miR-221 and miR-222 for use in the treatment of multiple myeloma.

In a preferred embodiment, said inhibitors are for use in the treatment of TC2 or TC4 multiple myeloma patient subsets.

The inhibitors can be used alone (only for miR-221 or only for miR-222) or in combination, in the absence of systemic toxicity. Their combined use provides a mean for higher anti-tumor activity.

Novel inhibitors of miR-221 and miR-222, namely LNA-i-miR-221 and LNA-i-miR-222, are also objects of the present invention.

A preferred embodiment of the present invention is the use of LNA-i-miR-221 or LNA-i-miR-222 or a combination thereof for inhibiting miR-221 and/or miR-222.

In a more preferred embodiment, LNA-i-miR-221 or LNA-i-miR-222 or a combination thereof are for use in the treatment of multiple myeloma.

The inhibitors for use in the present invention can be administered as a medicament, i.e. a pharmaceutical composition. The composition contains at least one active ingredient of the present invention with a suitable carrier. Average quantities of the active ingredient may vary and in particular should be based upon the recommendations and prescription of a qualified physician.

It is therefore an object of the present invention, a pharmaceutical composition comprising inhibitors of miR-221 and miR-222 as active ingredients for the treatment of multiple myeloma.

A pharmaceutical composition comprising LNA-i-miR-221 or LNA-i-miR-222, or a combination thereof, is also an object of the present invention.

In a preferred embodiment of the present invention, said pharmaceutical composition is administered to TC2 or TC4 multiple myeloma patients.

The pharmaceutical composition according to the present invention contains, along with the active ingredient, at least one pharmaceutically acceptable vehicle, or excipient. These may be particularly useful formulation coadjuvants, e.g. solubilising agents, dispersing agents, suspension agents, and emulsifying agents.

A preferred vehicle is a neutral lipid emulsion (NLE).

The inhibitors of the present invention can also be administered together with lipidic molecules such as cationic lipids, or peptides, or in the context of polymeric scaffolds, which can facilitate their delivery, according to the art. Another method to administer such inhibitors is by means of a suitable vector known for the administration of RNA or DNA. An exemplary vector is the adeno-associated vector (AAV), a well-known viral vector for administration of DNA in vivo. Indeed, all these methods and formulations are conventional and well known in the art and do not need any further explanation.

According to the present invention, the inhibitors can be administered as a medicament to a subject suffering from multiple myeloma by conventional methods.

Conveniently, said medicament is in the form of a preparation for intravenous administration but other forms are equally suitable for carrying out the present invention. The person skilled in the art will decide the effective time of administration, depending on the patient's conditions, degree of severity of the disease, response of the patient and any other clinical parameter within the general knowledge of this matter. Reference can be made to Remington's Pharmaceutical Sciences Handbook, last edition.

In vivo experiments have been performed by intraperitoneal administration since it is convenient for the experimental setting. However, intraperitoneal administration is not much suitable for clinical practice, where an intravenous administration is instead preferred. Intraperitoneal route is considered almost equivalent to the intravenous route due to the almost total blood clearance of intraperitoneally administered biomolecules.

According to the administration route chosen, the compositions will be in solid or liquid form, suitable for oral, parenteral, or intravenous administration.

Gene therapy is also another embodiment.

The following examples further illustrate the invention.

EXAMPLES

Materials and Methods

Cell lines

Human myeloma cell lines U266 and KMS34, and KMM1 were cultured in Iscove's modified Dulbecco's medium (IMDM) while OPM2, NCI-H929, and RPMI-8226 were grown in RPMI-1640 medium (Gibco®, Life Technologies, Carlsbad, Calif.) as previously described. Briefly, cultures were supplemented with 10% fetal bovine serum (Lonza Group Ltd., Switzerland), 100 U/ml penicillin, and 100 mg/ml streptomycin (Gibco®, Life Technologies) at 37° C. in a 5% $CO_2$ atmosphere.

In vitro Transfection of MM Cells by Synthetic miR-221/222 Mimics or Inhibitors

To transfect MM cell lines we used 100 nM of pre-miRNAs (miRs) or anti-miR inhibitors (i-miRs) (Life Technologies) using the Neon® Transfection System (Life Technologies) (see example 3). In a further example in vitro (see example 6), newly designed LNA-inhibitors (LNA-i-miR-221 and LNA-i-miR-222) have been used. Non-targeting pre-miRs or miRs inhibitors (negative controls, NC) were used at the same concentrations as negative controls. Cells were electroporated with scrambled oligonucleotide (miR-NC or anti-miR-NC) or synthetic miRs or anti-miRs at a final concentration of 100 nM, as previously described (36). Cells were collected and processed for quantitative real time PCR (Q-RT-PCR) (TaqMan miRNA assays, Applied Biosystems), immunoblotting (WB), proliferation assay (Trypan blue exclusion assay, BrdU incorporation, caspase activation) and cell cycle analysis by flow cytometry at different time points after transfection (24, 48, 72 and 96 h).

Cell Proliferation Assays

For cell proliferation analysis, $1.5 \times 10^5$ MM cells were plated in 6 well plates, electroporated with synthetic miR-221 and/or miR-222 or with miR-inhibitors (i-miR) or NC, and then harvested and counted at 24-hour intervals using a Trypan Blue-excluding viable cells assay. Each sample was performed in triplicate. Bromouridine (BrdU) uptake assay was performed by measuring the incorporation of BrdU into newly synthesized DNA strands using the DELFIA cell proliferation kit (Perkin-Elmer, Waltham, Mass.) according to the manufacturer's instructions. Briefly, after transfection with miRs, or i-miRs or NC, $1 \times 10^4$ cells were plated in 96 well. 1 µM BrdU was added at 24 hours intervals. BrdU-incorporation was measured by time-resolved fluorescence of a europium-chelate on a Wallac Victor$^2$ multilabel counter (Perkin-Elmer, Waltham, Mass.). All assays were repeated twice in triplicates.

Quantitative Real-Time Amplification (qPCR) of miRNAs and mRNAs

For qPCR, 15 ng of total RNA, prepared with the TRIzol® Reagent (Invitrogen) according to manufacturer's instructions, underwent reverse transcription by the Taq-Man® MicroRNA RT Kit or High Capacity cDNA Reverse Transcription Kit (Life Technologies) and specific miRNA or mRNA primers, according to the manufacturer's instructions. Real-time PCR was performed using TaqMan® MicroRNA Assays together with the TaqMan®Fast Universal PCR Master Mix on a ViiA7 System (Life Technologies). All of the RNA samples were normalized on the basis of the RNU44 (assay ID 001094) or GAPDH (assay ID Hs03929097_g1). The miR or mRNA expression was relatively quantified using the 2-ΔΔCt method (Applied Biosystems User Bulletin No. 2), and expressed as the relative quantity of target miRNA or mRNA normalized to the RNU44 or GAPDH housekeeping gene, respectively. Comparative real-time polymerase chain reaction (RT-PCR) was performed in quadruplicate, including no-template controls. Relative expression was calculated using the comparative cross threshold (Ct) method.

Immunoblotting

SDS-PAGE and Western Blotting (WB) were performed according to standard protocols. Briefly, cells were lysed in lysis buffer containing 15 mM Tris/HCl pH 7.5, 120 mM NaCl, 25 mM KCl, 1 mM EDTA, 0.5% Triton 100, Halt Protease Inhibitor Single-Use cocktail (100×, Thermo Scientific). Whole cells lysates (50 µg per line) from transfected cell lines were separated using 4-12% Novex Bis-Tris SDS-acrylamide gels (Invitrogen), electro-transferred on Nitrocellulose membranes (Bio-Rad), and immunoblotted with following antibodies: p27kip1 (SX53G8.5) mouse mAb (Cell Signaling), PTEN (A2B1) (Santa Cruz), Phospho-AKT (Ser473) rabbit mAb (Cell Signaling), AKT (pan, 11E7) rabbit mAB (Cell Signaling), Phospho-p44/42 MAPK (Erk1/2) (Thr202/Tyr204) rabbit mAb (Cell Signaling), p44/42 MAPK (Erk1/2) (Thr202/Tyr204) rabbit mAb (Cell Signaling), γ-Tubulin antibody (C-20) goat polyclonal (Santa Cruz). Membranes was washed 3 times in PBS-Tween, and then incubated with a secondary antiboby conjugated with horseradish peroxidase in 0.5% milk for 2 hours at room temperature. Chemiluminescence was detected using Pierce ECL Western Blotting Substrate (ID 32109, Pierce). Intensity signal was detected by Quantity One Analyzing System (Bio-Rad).

Cell Cycle Phase Distribution Analysis

Electroporated MM cells were plated in 6-well plates ($0.5 \times 10^6$ cells/ml) and cultured for 24, 48, 72, and 96 hours. At each time, cells were collected, washed twice in ice/cold 1×PBS and fixed by incubation in 70% ice/cold ethanol at 20° C. o.n. Before cytofluorimetric analysis, $5 \times 10^5$ cells were washed twice in 1×PBS and stained in 10 mg/ml 7-AAD, 100 mg/ml RNase, 0.05% Nonidet P-40 for 5 hours at room temperature in the dark. Cell cycle profiles were determined using MOD-FIT software (Verity Software House, Topshem, Me., USA) on a FACScan flow cytometer (Becton Dickinson, San Jose, Calif., USA).

Gene-Expression Profiling

Gene expression profiles were obtained from OPM2 cells after transfection with i-miR-221/222 or NC in 3 parallel experiments. 24 hours after transfection cells were collected and used for total RNA (tRNA) extraction by Trizol lysis and column purification with RNeasy kit (Qiagen, Hilden, Germany). A total of 300 ng RNA were used as starting material for preparing the hybridization target by using the Ambion® WT Expression Kit (Ambion, Life Technologies). The integrity, quality and quantity of tRNA were assessed by the Agilent Bioanalyzer 2100 (Agilent Technologies, Santa Clara, Calif.) and NanoDrop 1000 Spectrophotometer (Thermo Scientific, Wilmington, Del.). The amplification of cRNA, the clean up and the fragmentation was performed according to the Affymetrix's procedures. Microarray data was generated by Human GeneChip 1.0 ST (Affymetrix Inc., Santa Clara, Calif.) containing 764,885 distinct probes that interrogate 28,869 well-annotated genes. Arrays were scanned with an Affymetrix GeneChip Scanner 3000.

Raw data produced by the Affymetrix Platform (i.e. CEL files) were first processed using Affymetrix Expression Console (EC). Pre-processing phase was performed according to Affymetrix guidelines and micro-CS software. Raw data were normalized using probe logarithmic intensity error (PLIER) algorithm coupled to quantile normalization. Annotation of data was also performed using Affymetrix Provided Libraries and EC version 1.1. Differential expression was assessed using a linear model method. P-values were adjusted for multiple testing using the Benjamini and Hochberg method. Tests were considered to be significant for adjusted $P<0.05$. Clustering and fold change (FC) analysis were done using the dChip software comparing relative gene expression of scrambled-oligonucleotide transfected cells versus miR-221/222 inhibitors. For each pair of compared samples we calculated FC as follows: $FC=\log_2$(anti-miR-221/222 versus NC). The genes lists filtered for fold change +0.5 were imported into Ingenuity Pathway Analysis (IPA) software to perform core analysis (IPA, Redwood, Calif.).

Animals and in vivo Models of Human MM

Male CB-17 severe combined immunodeficient (SCID) mice (6- to 8-weeks old; Harlan Laboratories, Inc., Indianapolis) were housed and monitored in our Animal Research Facility. All experimental procedures and protocols had been approved by the Institutional Ethical Committee (Magna Graecia University) and conducted according to protocols approved by the National Directorate of Veterinary Services (Italy). In accordance with institutional guidelines, mice were sacrificed when their tumors reached 2 cm in diameter or in the event of paralysis or major compromise in their quality of life, to prevent unnecessary suffering. For our study, we used MM xenografts in SCID mice. For this model, mice were subcutaneously inoculated in the interscapular area with $1 \times 10^6$ MM cells in 100 µL RPMI-1640 medium. The animal treatment was initiated after the detection of palpable tumors, approximately 2 weeks following MM cells injection with 1 mg/kg per mouse of mirVana custom inhibitors (Life Technologies): i-miR-221, or i-miR-222, or together i-miR-221/222, or NC as control (see example 5).

In a further in vivo experiment (see example 7), the LNA-i-miR-221 has been used, which has the sequence +C*A*G*+A*+C*A*+A*T*+G*T*+A*+G*C, where letters with symbol "+" indicate the positions of LNA and symbol "*" indicates phosphorothioate bonds.

The tumor sizes were assessed as previously described. Administration of miRNAs inhibitors was performed as unformulated agents or formulated by the use of the neutral lipid emulsion (NLE) (MaxSuppressor in vivo RNA LANCEr II, BIOO Scientific, Austin, Tex.) according to the manufacturer's instructions. Treatments were performed intratumorally (i.t.) every two days for a total of seven injections. Tumors were then collected and placed in either 10% formalin for histology or in RNAlater® for RNA isolation or stored at −80° C. for protein analysis.

Histology and Immunohistochemistry

Retrieved tumors from animals were immediately fixed by immersion in 4% buffered formaldehyde for 24 h at 4° C., washed, dehydrated, and embedded in paraffin. For the light microscopy analysis, sections were cut (4 µm), mounted on poly-lysine slides, and stained with H&E. For immunohistochemistry staining, 2 µm thick sections were dried in a 60° C. oven overnight. The sections were placed in Bond Max Automated Immunohistochemistry, according to the following protocol. First, tissues were deparaffinized and pretreated with the Epitope Retrieval Solution 2 (EDTA-buffer pH8.8) at 98° C. for 20 min. After washing steps, peroxidase blocking was carried out for 10 min using the Bond Polymer Refine. Tissues were again washed and then incubated with the primary antibody directed against Ki-67 (Dako, clone: MIB-1; 1:150) or, caspase-3 (NOVOCASTRA, clone: JHM62; 1:500). Subsequently, tissues were incubated with polymer for 10 min and developed with DAB-Chromogen for 10 min. Slides were counterstained with hematoxylin.

Statistical Analysis

All in vitro experiments were repeated at least 3 times and performed in triplicate; a representative experiment was showed in figures. Statistical significances of differences were determined using Student's t test, with minimal level of significance specified as $P<0.05$. Statistical significance of the in vivo growth inhibition observed in miRNAs inhibitor-treated mice compared with control group was determined using Student's t test. The minimal level of significance was specified as $P<0.05$. All statistical analyses were determined using GraphPad software (www.graphpad.com). Graphs were obtained using Microsoft Office Excel tool.

Example 1

Expression of miR-221 and miR-222 in MM and PCL Patients and in MM Cell Lines

MiRNA profiles were investigated by microarray analysis among the different TC (Translocation/Cyclin) classified MM samples, referring to the data disclosed in Lionetti et al. (2009) (7).

The TC classification is made according to the presence of the recurrent IGH chromosomal translocations and cyclins D expression: TC1: patients characterized by the t(11;14) or t(6;14) translocation; TC2: patients showing low to moderate levels of the CCND1 gene in the absence of any primary IGH translocation; TC3: patients that do not fall into any of the other groups; TC4: patients showing high CCND2 levels and the presence of the t(4;14) translocation; TC5: patients with either the t(14;16) or the t(14;20) translocation (Hideshima et al., Blood 2004).

Figure 1:
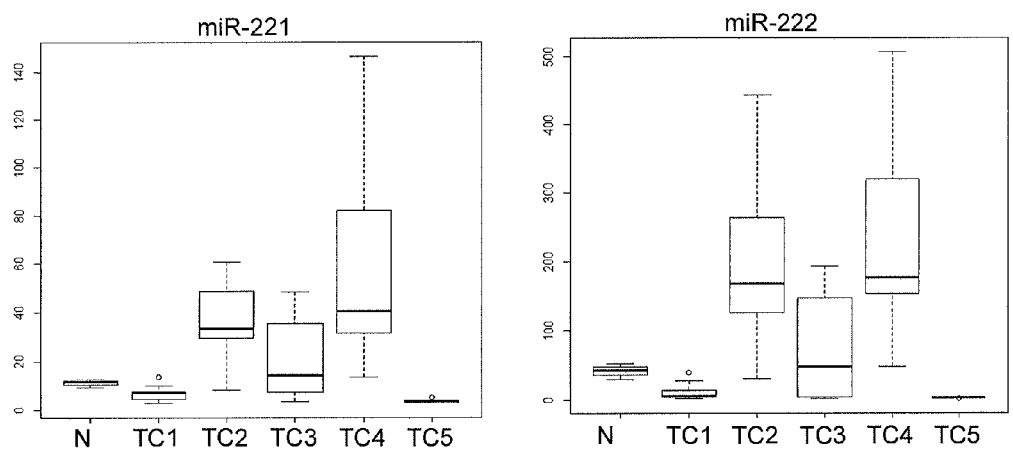
FIG. 1 shows miR-221 and miR-222 expression in MM patients and cell lines. MiR-221 and miR-222 are highly expressed in CD138+ malignant plasma cells derived from bone marrow aspirates of myeloma patients. Also myeloma cell lines established from myeloma patients express high levels of miR-221/222.
Figure 1:
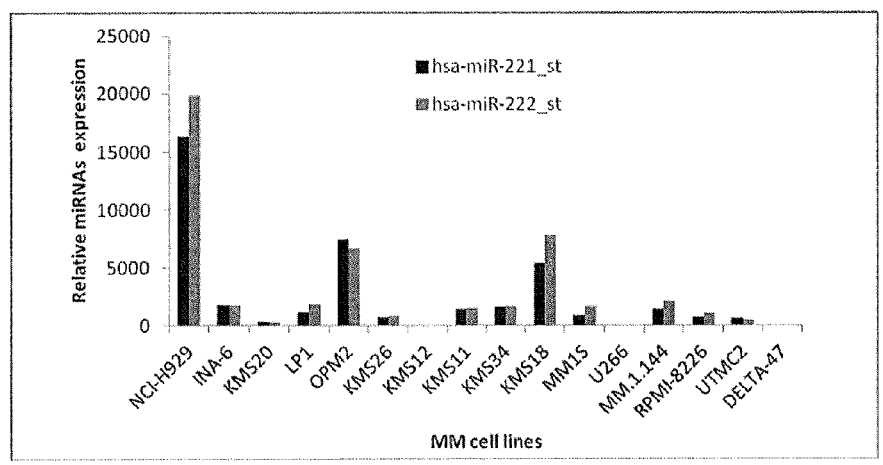

MiR-221/222 expression in TC2 and TC4 patient groups was found significantly higher, as assessed by SAM multi-class analysis (q-value=0) (FIG. 1A).

In parallel, by microarray miRNA profiling, evaluation of miR-221/222 expression in 16 MM cell lines (FIG. 1B) indicated different miR221/222 expression levels. Data on cell lines have been performed by RT-PCR, which produce quantitative assessment. It has to be considered that myeloma cell lines represent highly aggressive disease.

Among all tested MM cells, in our study we selected the U266 and RPMI-8226 cells (t(1;11) and t(1;14), respectively), with low miR-221/222 expression to evaluate the oncogenic role of these miRNAs and the OPM2 and NCI-H929 cells, both t(4;14) with moderate and high expression of both miRNAs respectively, to explore the anti-tumor activity of miR-221 and/or miR-222 inhibitors.

Example 2

In Vitro Enforced Expression of miR-221/222 in MM Cells

To investigate the role of synthetic miR-221 or miR-222 in MM, we first transfected U266 and RPMI-8226 cells, that constitutively express low levels of both miRNAs, with pre-miR-221 and pre-miR-222 mimics. MiR 221 and miR 222 levels were evaluated by q-RT-PCR and we observed increase of both miRs expression as compared to negative control 48, 72 and 96 hours after transfection. At the same time points no (U266) or weak (RPMI-8226) changes in cell number were observed in comparison to negative control, as well as alteration of cell proliferation by means of a cell proliferation assay.

Against, in transfected U266 cells cell cycle analysis revealed increase in the percentage of cells in S phase, starting from 48 h, becoming more marked at 72 h and decreasing at 96 h (FIG. 2A).

As miR-221/222 negatively regulate p27kip1 expression in different cell types, we evaluated if this modulation could occur in our experimental model. Western blot (WB) analysis of whole cell lysate showed a pronounced reduction of p27kip1 protein expression in miR-221/222-transfected cells: based on densitometric analysis p27 levels were more than 90% lower than controls at 48 h, beginning to raise towards basal levels at 72 h and 96 h (FIG. 2B, top). Targeting of p27kip1 protein by miR-221 and miR-222 was also tested in RPMI-8226 myeloma cells, expressing moderate levels of these miRNAs. Here, the increase of miRs 221 and 222 by means of the addiction of their synthetic precursors resulted in a marked reduction of p27kip1 protein, confirming the data obtained in the U266 cell line (FIG. 2B, bottom).

Expression levels of miR-221 and miR-222 have been correlated with those of p27kip1 mRNA as measured by microarray analysis in a dataset of primary myeloma patients. A significant inverse correlation between both miRNAs and p27kip1 transcript levels (Pearson product-moment correlation, $p<0.05$) further underlines the basic concept that miR-221/222 indeed negatively regulate p27kip1 producing an enhanced proliferative activity, as we have experimentally demonstrated.

Our findings thus clearly demonstrates that enforced expression of exogenous miR-221/222 exerts growth promoting activity and down-regulates p27kip1, a negative regulator of myeloma cell progression within the cell cycle.

Example 3

In Vitro Enforced Inhibition of miR-221/222 in MM Cells

As a complementary approach, we blocked miR-221/222 activity in OPM2 and NCI-H929 cells showing higher basal expression levels of this miRs by electroporation of both miR-221 and miR-222 inhibitors. FIG. 3 shows antiproliferative activity induced by miR-221/222 inhibitors in different MM cell lines assessed by BrdU incorporation.

To correlate this effect with the efficient inhibition of miRs-221/222 we evaluated the levels of single miRs by q-RT-PCR 24 hours from inhibitors transfection. An about 50% reduction of both miRs level was detected in OPM2 cells (FIG. 3B). As a consequence we observed a significant up-regulation of p27kip1 mRNA (FIG. 3C) and protein expression (at least 3-fold increase, FIG. 3D) 48 hours after transfection. Moreover, we evaluate the up-regulation of others validated miR-221/222 targets as well as PUMA, PTEN, and p57kip2 mRNAs in this MM cell line (FIG. 3C).

All together, these results demonstrate that synthetic miR-221/222 inhibitors activity involves modulation of validated targets. The specificity of their activity is particularly demonstrated by up-regulation of proteins, which are known as selective targets of miR-221/222.

Example 4

Effects of miR-221/222 Inhibition on the Whole Cell Transcriptome

We investigated the miR-221/222 inhibitors anti-MM activity at trascriptome level by performing gene expression analysis in OPM2 cells transfected with synthetic miR-221/222 inhibitors or NC.

To analyze higher-order influences on biological networks regulated by miR-221/222 inhibitors independently from predicted targets, fold change analysis was performed on the whole gene data sets. The lists obtained after fold change analysis (FC=±0.5) underwent Ingenuity pathway analysis (IPA). IPA analysis reveals that miR-221/222 inhibition, induces modulation in different biological functions as cell death, cell cycle, cellular growth and proliferation as well as cell-to-cell signaling and interaction (p-value<0.05). Moreover, the analysis of the relative impact of changes in mRNA levels (as a consequence of miR-221/222 inhibition) in the context of well-characterized pathways identified important signal transduction pathways (i.e. LPS/IL-1 mediated inhibition of RXR function (P-value 5.02E-04, LXR/RXR activation P-value 9.28E-03, and IL-10 signaling P-value 1.11E-02) as shown in FIG. 4A.

These findings suggested that RXR mediated pathways may have an important role in the anti-proliferative effect of MM cells as evidenced by in vitro experiments.

To examine this further, we looked at the mostly scored network designed for all the differentially expressed genes analyzed by IPA. Among the mostly interested networks, higher score was obtained for the networks illustrated in FIG.

4B. The higher scored network has two hub nodes: NFkB and P38MAPK-ERK1/2, while in the second high scored network the central node is represented by TNF.

The understanding of the molecular pathways correlated with the anti-tumor effect of miR-221/222 inhibitors is of major value for the identification of early biomarkers of anti-tumor activity predictive of long-term therapeutical benefit, which may be relevant for treatment personalization.

Example 5

Inhibition of MM Xenografts in SCID Mice by Intratumoral Delivery of miR-221/222 Inhibitors We next investigated the effect of anti-miR-221 and/or miR-222 inhibitors treatment against t(4;14) MM xenograft in SCID/NOD mice.

When OPM2 MM tumors became palpable, animals were randomized and intratumorally treated with miR-221 and/or miR-222 inhibitors (mirVana custom inhibitors; Life Technologies) or controls. Inhibitors were both administered as unformulated agents or formulated with NLE particles that have been demonstrated to successfully deliver oligonucleotides in vivo.

In a first series of experiment, we found a significant ($P<0.05$) inhibition of tumor growth in mice treated with miR-221/222 inhibitors at similar extent for both NLE-i-miR221/222 and PBS-i-miR221/222 (FIG. 5A).

By the use of NLE-formulated i-miR-221 or i-miR-222, we observed higher activity of i-miR-221 rather than for i-miR-222 (FIG. 5B).

We then studied the activity of i-miR-221 even as unformulated agent and we confirmed its anti-MM effect in xenografted mice (FIG. 5C).

Importantly, by q-RT-PCR analysis of retrieved tumors from animal treated with miR-221 inhibitors, we found a >60% reduction of miR-221 and miR-222 expression (FIG. 6A), suggesting a correlation between miR221/222 shared target down-regulation and anti-MM effects.

Moreover, histology and immunohistochemistry analysis showed large areas of necrosis with abundant nuclear debris ("dustlike" nuclear fragments, FIG. 6B) in miR-221 inhibitor treated xenografts. MM cells exhibited cleaved caspase-3 and lower Ki-67 expression, indicating that miR-221 inhibitors induced anti-proliferative activity and triggered apoptosis in MM xenografts in vivo.

Finally, we demonstrated up-regulation of p27kip1 and PTEN validated miR-221/222 target mRNAs (FIG. 6C) and proteins (FIG. 6D) by q-RT-PCR and Western blotting, respectively. Notably, inhibition of miR-221/222 significantly reduced the phosphorylation of AKT, a down-stream target of PTEN and key mediator of tumor cell survival (FIG. 6E), suggesting that the in vivo anti-MM activity of i-miR-221 is related to PTEN up-regulation and AKT activation impairment within tumors. Interestingly, the inhibition of miR-221/222 in vivo considerably reduced the p-ERK levels while total ERK1/2 was unaffected. This result appears of major interest taking into account the role of ERK1/2 and AKT in the process of cell proliferation and survival.

Taken together, these results show that the miR-221 inhibitors modulate different genes involved in proliferation and carcinogenesis pathways thus demonstrating the potential and specific anti-MM effectiveness of miR-221 inhibitors.

Example 6

Modified LNA Oligonucleotides Antagonize miRs Function in MM Cells In Vitro

To assess the specific activity of the new designed LNA-inhibitors (LNA-i-miR-221 and LNA-i-miR-222) in absence of cell death for induced toxicity, we evaluated the modulation of p27kip1 and p57kip2, miR-221/222 targets, at different inhibitor concentrations in OPM2 cells.

MiR-221 inhibitor blocks specifically the repression of the miR-221/222 targets 24 h after electroporation in a concentration-dependent manner. As shown in FIG. 7A, most p27kip1 up-regulation occurred 24 hours after 30 nM of miR-221 inhibitor electroporation, while miR-222 inhibitor showed a similar p27kip1 up-regulation at each concentration used but with transient effect that completely disappeared after 72 hours from electroporation.

Therefore, the new LNA-inhibitors efficiently modulate miR-221/222 targets.

This experiment provides the first evidence of biological activity produced by the new LNA-inhibitors.

Example 7

In Vivo Antitumor Activity of Modified LNA miR-221 Inhibitor

We used LNA-i-miR-221 for systemic treatment of MM xenografts mouse model. OPM2 cells were engrafted as described in example 5.

We administered by intraperitoneal injection of saline LNA-i-miR-221 or LNA-i-miR-221-NC (a scramble oligonucleotide with sequence 5'CTGAGAAAGTACC3' (SEQ ID NO: 3) used as control) compound following the schedule: 25 mg/kg at day 1 and 25 mg/kg at day 8. We stopped the animal treatment because the NC tumors enriched>2000 mm$^3$ of volume.

We detected a significant ($P<0.05$) inhibition of tumor growth in mice treated with LNA-i-miR-221 after only two single doses of compound in a similar extent that for intratumors treatments compared to controls animal group. (FIG. 7B)

This experiment demonstrates that the new LNA inhibitors are suitable for clinical application since they exert systemic antitumor activity, the goal to be reached in myeloma patients.

REFERENCES

1. Anderson K C, Carrasco R D. Pathogenesis of myeloma. Annu Rev Pathol. 2011; 6:249-74.
2. Rajkumar S V. Treatment of multiple myeloma. Nat Rev Clin Oncol. 2011; 8:479-91.
3. Lonial S, Mitsiades C S, Richardson P G. Treatment options for relapsed and refractory multiple myeloma. Clin Cancer Res. 2011; 17:1264-77.
4. Kapoor P, Rajkumar S V. Update on risk stratification and treatment of newly diagnosed multiple myeloma. Int J Hematol. 2011.
5. Tassone P, Tagliaferri P, Rossi M, Gaspari M, Terracciano R, Venuta S. Genetics and molecular profiling of multiple myeloma: novel tools for clinical management? Eur J Cancer. 2006; 42:1530-8.
6. Palumbo A, Anderson K. Multiple myeloma. N Engl J Med. 2011; 364:1046-60.

7. Lionetti M, Biasiolo M, Agnelli L, Todoerti K, Mosca L, Fabris S, et al. Identification of microRNA expression patterns and definition of a microRNA/mRNA regulatory network in distinct molecular groups of multiple myeloma. Blood. 2009; 114:e20-6.
8. Pichiorri F, De Luca L, Aqeilan R I. MicroRNAs: New Players in Multiple Myeloma. Frontiers in genetics. 2011; 2:22.
9. Benetatos L, Vartholomatos G. Deregulated microRNAs in multiple myeloma. Cancer. 2011.
10. Bartel D P. MicroRNAs: genomics, biogenesis, mechanism, and function. Cell. 2004; 116:281-97.
11. Friedman R C, Farh K K, Burge C B, Bartel D P. Most mammalian mRNAs are conserved targets of microRNAs. Genome Res. 2009; 19:92-105.
12. Ambros V. The functions of animal microRNAs. Nature. 2004; 431:350-5.
13. He L, Hannon G J. MicroRNAs: small RNAs with a big role in gene regulation. Nat Rev Genet. 2004; 5:522-31.
14. Cahn G A, Sevignani C, Dumitru C D, Hyslop T, Noch E, Yendamuri S, et al. Human microRNA genes are frequently located at fragile sites and genomic regions involved in cancers. Proc Natl Acad Sci USA. 2004; 101:2999-3004.
15. Croce C M. Causes and consequences of microRNA dysregulation in cancer. Nat Rev Genet. 2009; 10:704-14.
16. Esquela-Kerscher A, Slack F J. Oncomirs—microRNAs with a role in cancer. Nat Rev Cancer. 2006; 6:259-69.
17. Cahn G A, Croce C M. MicroRNAs and chromosomal abnormalities in cancer cells. Oncogene. 2006; 25:6202-10.
18. Garzon R, Marcucci G, Croce C M. Targeting microRNAs in cancer: rationale, strategies and challenges. Nat Rev Drug Discov. 2010; 9:775-89.
19. Frenquelli M, Muzio M, Scielzo C, Fazi C, Scarfo L, Rossi C, et al. MicroRNA and proliferation control in chronic lymphocytic leukemia: functional relationship between miR-221/222 cluster and p27. Blood. 2010; 115:3949-59.
20. le Sage C, Nagel R, Egan D A, Schrier M, Mesman E, Mangiola A, et al. Regulation of the p27(Kip1) tumor suppressor by miR-221 and miR-222 promotes cancer cell proliferation. The EMBO journal. 2007; 26:3699-708.
21. Medina R, Zaidi S K, Liu C G, Stein J L, van Wijnen A J, Croce C M, et al. MicroRNAs 221 and 222 bypass quiescence and compromise cell survival. Cancer Res. 2008; 68:2773-80.
22. Garofalo M, Di Leva G, Romano G, Nuovo G, Suh S S, Ngankeu A, et al. miR-221 &222 regulate TRAIL resistance and enhance tumorigenicity through PTEN and TIMP3 downregulation. Cancer Cell. 2009; 16:498-509.
23. Chun-Zhi Z, Lei H, An-Ling Z, Yan-Chao F, Xiao Y, Guang-Xiu W, et al. MicroRNA-221 and microRNA-222 regulate gastric carcinoma cell proliferation and radioresistance by targeting PTEN. BMC cancer. 2010; 10:367.
24. Pineau P, Volinia S, McJunkin K, Marchio A, Battiston C, Terris B, et al. miR-221 overexpression contributes to liver tumorigenesis. Proc Natl Acad Sci USA. 2010; 107:264-9.
25. Galardi S, Mercatelli N, Giorda E, Massalini S, Frajese G V, Ciafre S A, et al. miR-221 and miR-222 expression affects the proliferation potential of human prostate carcinoma cell lines by targeting p27Kip1. J Biol Chem. 2007; 282:23716-24.
26. Livak K J, Schmittgen T D. Analysis of relative gene expression data using real-time quantitative PCR and the 2(-Delta Delta C(T)) Method. Methods. 2001; 25:402-8.
27. Zhang C, Kang C, You Y, Pu P, Yang W, Zhao P, et al. Co-suppression of miR-221/222 cluster suppresses human glioma cell growth by targeting p27kip1 in vitro and in vivo. International journal of oncology. 2009; 34:1653-60.
28. Wiggins J F, Ruffino L, Kelnar K, Omotola M, Patrawala L, Brown D, et al. Development of a lung cancer therapeutic based on the tumor suppressor microRNA-34. Cancer Res. 2010; 70:5923-30.
29. Trang P, Wiggins J F, Daige C L, Cho C, Omotola M, Brown D, et al. Systemic delivery of tumor suppressor microRNA mimics using a neutral lipid emulsion inhibits lung tumors in mice. Mol Ther. 2011; 19:1116-22.
30. Jimenez-Zepeda V H, Dominguez-Martinez V J. Plasma cell leukemia: a highly aggressive monoclonal gammopathy with a very poor prognosis. Int J Hematol. 2009; 89:259-68.
31. Tiedemann R E, Gonzalez-Paz N, Kyle R A, Santana-Davila R, Price-Troska T, Van Wier S A, et al. Genetic aberrations and survival in plasma cell leukemia. Leukemia. 2008; 22:1044-52.
32. Lloveras E, Granada I, Zamora L, Espinet B, Florensa L, Besses C, et al. Cytogenetic and fluorescence in situ hybridization studies in 60 patients with multiple myeloma and plasma cell leukemia. Cancer Genet Cytogenet. 2004; 148:71-6.
33. Gertz M A, Lacy M Q, Dispenzieri A, Greipp P R, Litzow M R, Henderson K J, et al. Clinical implications of t(11; 14)(q13;q32), t(4;14)(p16.3;q32), and −17p13 in myeloma patients treated with high-dose therapy. Blood. 2005; 106: 2837-40.
34. Roccaro A M, Sacco A, Thompson B, Leleu X, Azab A K, Azab F, et al. MicroRNAs 15a and 16 regulate tumor proliferation in multiple myeloma. Blood. 2009; 113:6669-80.
35. Pichiorri F, Suh S S, Rocci A, De Luca L, Taccioli C, Santhanam R, et al. Downregulation of p53-inducible microRNAs 192, 194, and 215 impairs the p53/MDM2 autoregulatory loop in multiple myeloma development. Cancer Cell. 2010; 18:367-81.
36. Di Martino M T, Leone E, Amodio N, Foresta U, Lionetti M, Pitari M R, Cantafio M E, Gullà A, Conforti F, Morelli E, Tomaino V, Rossi M, Negrini M, Ferrarini M, Caraglia M, Shammas M A, Munshi N C, Anderson K C, Neri A, Tagliaferri P, Tassone P. Synthetic miR-34a Mimics as a Novel Therapeutic Agent for Multiple Myeloma: In Vitro and In Vivo Evidence. Clin Cancer Res. 2012 Nov. 15; 18(22):6260-6270.

The invention claimed is:

1. A method for treating multiple myeloma, comprising administering to a patient having multiple myeloma an inhibitor of miR-221 and miR-222 having the nucleic acid sequence +C*A*G*+A*+C*A*+A*T*+G*T*+A*+G*C (SEQ ID NO: 1) or C*+A*+G*+A*T*+G*T*+A*+G*C (SEQ ID NO: 2), wherein the symbol + indicates the position of a locked nucleic acid (LNA), and the symbol * indicates the position of a phosphorothioate bond, thereby treating multiple myeloma in the patient.

2. The method according to claim 1, wherein the multiple myeloma patient is selected from the group consisting of the TC2 multiple myeloma subset and the TC4 multiple myeloma subset.

3. A compound, comprising the nucleic acid sequence +C*A*G*+A*+C*A*+A*T*+G*T*+A*+G*C (SEQ ID NO: 1), wherein the symbol + indicates the position of a locked nucleic acid (LNA) and symbol * indicates the position of a phosphorothioate bond.

4. A compound, comprising the nucleic acid sequence C*+A*+G*+A*T*+G*T*+A*+G*C (SEQ ID NO: 2), wherein the symbol + indicates the position of a locked nucleic acid (LNA) and the symbol * indicates the position of a phosphorothioate bond.

5. A pharmaceutical composition, comprising the compound according to claim 3 and at least one pharmaceutically acceptable vehicle, at least one excipient, or at least one pharmaceutically acceptable vehicle and at least one excipient.

6. The pharmaceutical composition of claim 5, wherein said vehicle is a neutral lipid emulsion (NLE).

7. A pharmaceutical composition, comprising the compound according to claim 4 and at least one pharmaceutically acceptable vehicle, at least one excipient, or at least one pharmaceutically acceptable vehicle and at least one excipient.

8. The pharmaceutical composition of claim 7 wherein said vehicle is a neutral lipid emulsion (NLE).

9. A method for treating multiple myeloma, comprising administering the pharmaceutical composition of claim 5 to a patient having multiple myeloma, thereby treating multiple myeloma in the patient.

10. The method according to claim 9, wherein the patient is a TC2 multiple myeloma patient.

11. The method according to claim 9, wherein the patient is a TC4 multiple myeloma patient.

12. The method according to claim 9, wherein the administering comprises intravenously administering.

13. A method for treating multiple myeloma, comprising administering the pharmaceutical composition of claim 7 to a patient having multiple myeloma, thereby treating multiple myeloma in the patient.

14. The method according to claim 13, wherein patient is a TC2 multiple myeloma patient.

15. The method according to claim 13, wherein the patient is a TC4 multiple myeloma patient.

16. The method according to claim 13, wherein the administering comprises intravenously administering.

* * * * *